US011523793B2

(12) United States Patent
Rogers et al.

(10) Patent No.: US 11,523,793 B2
(45) Date of Patent: Dec. 13, 2022

(54) METHODS FOR X-RAY TUBE ROTORS WITH SPEED AND/OR POSITION CONTROL

(71) Applicant: GE Precision Healthcare LLC, Milwaukee, WI (US)

(72) Inventors: Carey Rogers, Waukesha, WI (US); Vasile Bogdan Neculaes, Niskayuna, NY (US); Nidhishri Tapadia, Arvada, CO (US); Andrew Thomas Cross, Waterford, NY (US); Uwe Wiedmann, Clifton Park, NY (US)

(73) Assignee: GE Precision Healthcare LLC, Milwaukee, WI (US)

( * ) Notice: Subject to any disclaimer, the term of this patent is extended or adjusted under 35 U.S.C. 154(b) by 312 days.

(21) Appl. No.: 16/869,999

(22) Filed: May 8, 2020

(65) Prior Publication Data

US 2021/0345983 A1  Nov. 11, 2021

(51) Int. Cl.
| *A61B 6/00* | (2006.01) |
| *H01J 35/00* | (2006.01) |
| *A61B 6/03* | (2006.01) |
| *H02P 23/20* | (2016.01) |
| *H01J 35/10* | (2006.01) |
| *H01J 35/08* | (2006.01) |

(52) U.S. Cl.
CPC .............. *A61B 6/547* (2013.01); *A61B 6/035* (2013.01); *A61B 6/4476* (2013.01); *H01J 35/10* (2013.01); *H02P 23/20* (2016.02); *H01J 35/08* (2013.01)

(58) Field of Classification Search
CPC ...... H01J 35/103; H01J 35/1017; H01J 35/10; H01J 35/101
See application file for complete search history.

(56) References Cited

U.S. PATENT DOCUMENTS

| 3,663,075 A | 5/1972 | Kronenberg |
| 4,811,375 A | 3/1989 | Klostermann |
| 5,090,041 A | 2/1992 | Furbee |
| 5,506,881 A | 4/1996 | Ono et al. |
| 5,566,219 A | 10/1996 | Vogler |
| 6,011,829 A | 1/2000 | Panasik |
| 6,118,203 A | 9/2000 | Hansen |
| 6,198,803 B1 | 3/2001 | Osama et al. |

(Continued)

FOREIGN PATENT DOCUMENTS

| DE | 102011077746 A1 | 4/2012 |
| EP | 0676911 A1 | 10/1995 |

(Continued)

OTHER PUBLICATIONS

"Euclidean vector," Wikipedia Website, Available Online at https://en.wikipedia.org/wiki/Euclidean_vector, Nov. 8, 2001, 18 pages.

(Continued)

*Primary Examiner* — Dani Fox

(57) ABSTRACT

Various methods and systems are provided for an x-ray imaging system. In one example, a method for decelerating a rotor of an x-ray tube of an imaging system includes controlling and/or monitoring a speed and position of the rotor, passing the rotor through a first position where a force exerted on the rotor, is less than Earth's gravitational pull, the force due to a combination of gravity and radial acceleration, and initiating a predefined deceleration profile to decelerate the rotor to a halt when the x-ray tube passes through the first position.

12 Claims, 25 Drawing Sheets

(56) References Cited

U.S. PATENT DOCUMENTS

| | | |
|---|---|---|
| 6,553,091 B2 | 4/2003 | Takanashi et al. |
| 6,570,960 B1 | 5/2003 | Kuzniar et al. |
| 6,700,947 B2 | 3/2004 | Oshima et al. |
| 6,751,291 B2 | 6/2004 | Nakamuta et al. |
| 6,873,683 B2 | 3/2005 | Tiwari et al. |
| 7,202,580 B2 | 4/2007 | Yokoyama et al. |
| 7,406,149 B2 | 7/2008 | Yokoyama et al. |
| 7,519,158 B2 | 4/2009 | Gadre et al. |
| 8,054,943 B2 | 11/2011 | Danyluk |
| 9,530,609 B2 | 12/2016 | Deuringer et al. |
| 10,626,921 B2 | 4/2020 | Gorilla |
| 2005/0100132 A1* | 5/2005 | Block ............... H01J 35/10 378/124 |
| 2011/0135065 A1* | 6/2011 | Danyluk ............ H01J 35/1024 445/28 |
| 2015/0170870 A1 | 6/2015 | Jajtic et al. |
| 2017/0214279 A1 | 7/2017 | Smith et al. |
| 2018/0277330 A1 | 9/2018 | Nagesh et al. |
| 2019/0096625 A1 | 3/2019 | Heinke et al. |
| 2019/0162237 A1 | 5/2019 | Gorrilla |

FOREIGN PATENT DOCUMENTS

| | | |
|---|---|---|
| JP | S59060949 A | 4/1984 |
| JP | H06295691 A | 10/1994 |
| JP | 2000243595 A | 9/2000 |
| JP | 2001326095 A | 11/2001 |
| JP | 2002010608 A | 1/2002 |
| JP | 2004135433 A | 4/2004 |
| JP | 2007209194 A | 8/2007 |
| WO | 2009055284 A1 | 4/2009 |

OTHER PUBLICATIONS

Hirani, H. et al., "Hybrid (hydrodynamic + permanent magnetic) journal bearings," Sage Journals, vol. 221, No. 8, Aug. 2007, 12 pages.

Murray, J. et al., "Repair of EDM induced surface cracks by electron beam irradiation," Journal of Materials Processing Technology, vol. 212, No. 12, Dec. 2012, Available Online Aug. 7, 2012, 10 pages.

Shin, M., "Development and Evaluation of Two Novel Instruments for X-Ray Imaging," Doctor of Philosophy Dissertation, Department of Mechanical Engineering and the Commitee on Graduate Studies of Stanford University, Stanford University, Jun. 2015, 116 pages.

Marazani, T. et al., "Repair of cracks in metals: A review," Proceedings of the 14th Global Conference on Sustainable Manufacturing, Oct. 3, 2016, Stellenbosch, South Africa, 8 pages.

* cited by examiner

METHODS FOR X-RAY TUBE ROTORS WITH SPEED AND/OR POSITION CONTROL

FIELD

Embodiments of the subject matter disclosed herein relate to x-ray tubes and more particularly to permanent magnet x-ray assemblies.

BACKGROUND

X-ray systems may include an x-ray tube, a detector, and a support structure for the x-ray tube and the detector. In operation, an imaging table, on which an object is positioned, may be located between the x-ray tube and the detector. The x-ray tube typically emits radiation, such as x-rays, toward the object. The radiation passes through the object on the imaging table and impinges on the detector. As radiation passes through the object, internal structures of the object cause variances in the attenuation of the radiation received at the detector. The detector then emits data received, and the system translates the radiation variances into an image, which may be used to evaluate the internal structure of the object. The object may include, but is not limited to, a patient in a medical imaging procedure and an inanimate object as in, for instance, a package in an x-ray scanner or computed tomography (CT) package scanner.

X-ray tubes include a cathode and an anode located within a high-vacuum environment. The anode structure may be supported by one or more bearing members and is rotated for the purpose of distributing the heat generated at a focal spot. An induction motor may be employed to rotate the anode, the induction motor having a cylindrical rotor built into a cantilevered axle that supports a disc-shaped anode target and an iron stator structure with copper windings that surround an elongated neck of the x-ray tube. The rotor of the rotating anode assembly is driven by the stator. An x-ray tube cathode provides a focused electron beam that is accelerated across an anode-to-cathode vacuum gap and produces x-rays upon impact with the anode. Because of the high temperatures generated when the electron beam strikes the target, it is necessary to rotate the anode assembly at high rotational speed. Also, because the gantry assembly that includes the x-ray tube must spin with high rotational speed around a patient to provide good image quality, centripetal loads are high on the bearing assembly. This places stringent demands on the bearings and the material forming the anode structure, i.e., the anode target and the shaft supporting the target.

BRIEF DESCRIPTION

In one embodiment, a method for decelerating a rotor of an x-ray tube of an imaging system, includes controlling and/or monitoring a speed and position of the rotor, passing the rotor through a first position where a force exerted on the rotor, is less than Earth's gravitational pull, the force due to a combination of gravity and radial acceleration, and initiating a predefined deceleration profile to decelerate the rotor to a halt when the x-ray tube passes through the first position. In this way, rubbing between the shaft and the sleeve of a bearing assembly is circumvented or at least decreased as the rotor is decelerated to a halt. A useful life of the liquid bearing assembly is thereby prolonged. Furthermore, as another example, various operations contributing to enhanced image quality are enabled by accurate monitoring of rotor speed and position.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIGS. 5-6, 10-11, 17, 20, 23, and 26-28 are shown approximately to scale although other relative dimensions may be used.

DETAILED DESCRIPTION

Figure 1:
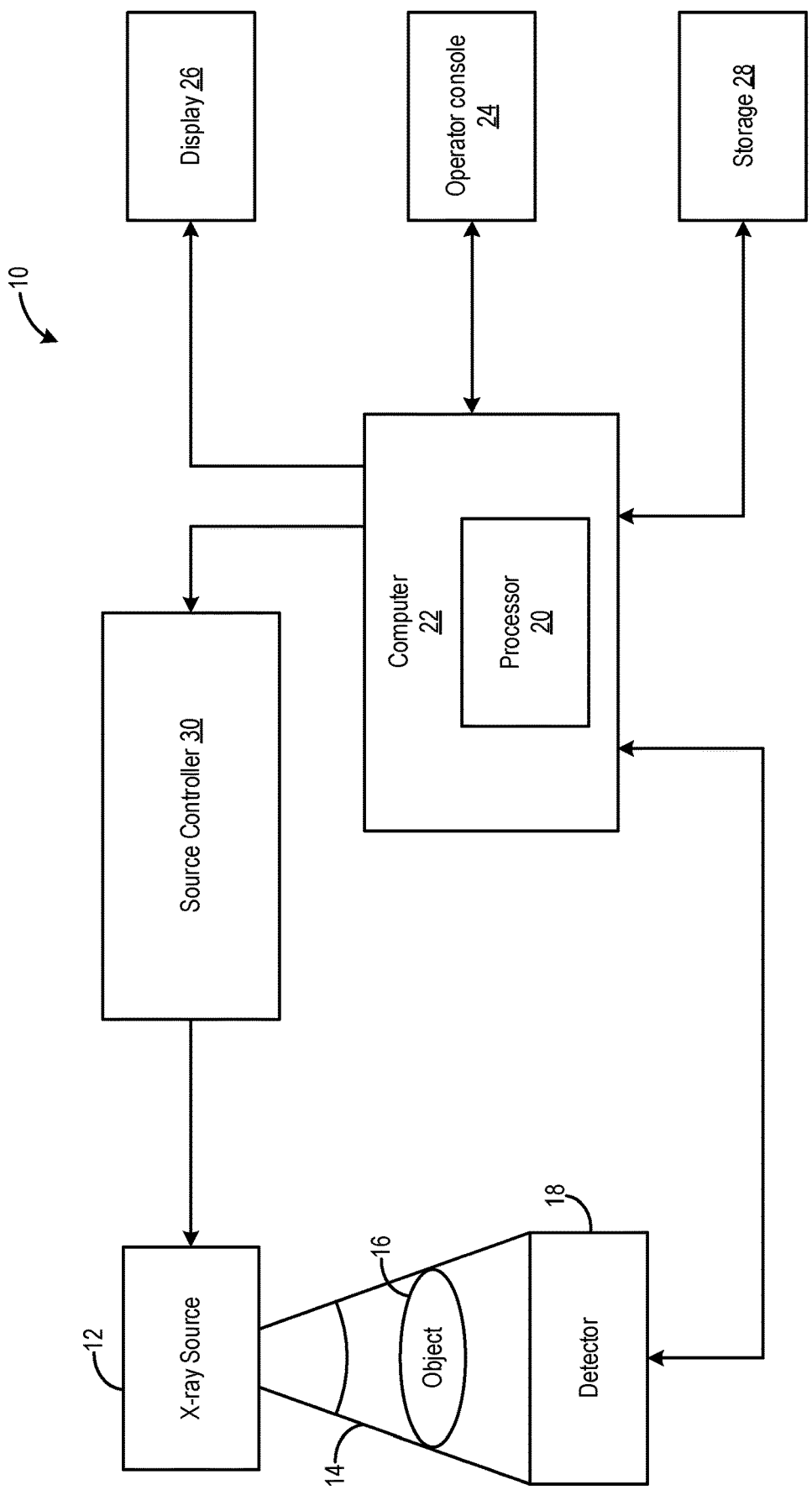
FIG. 1 shows a block diagram of an example of an imaging system.
Figure 2:
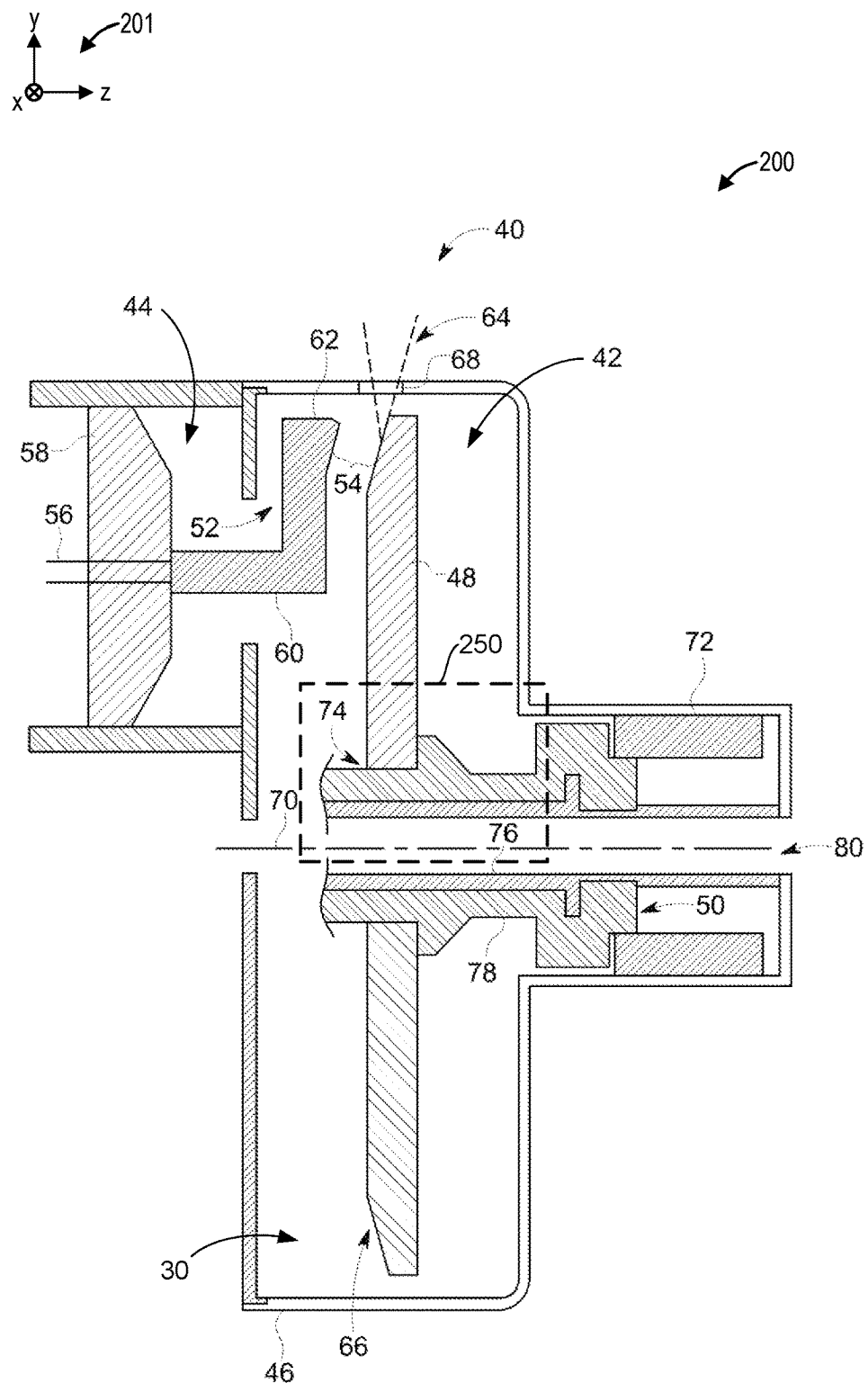
FIG. 2 shows a cross-sectional view of a portion of an x-ray tube which may be included in the imaging system of FIG. 1.
Figure 3:
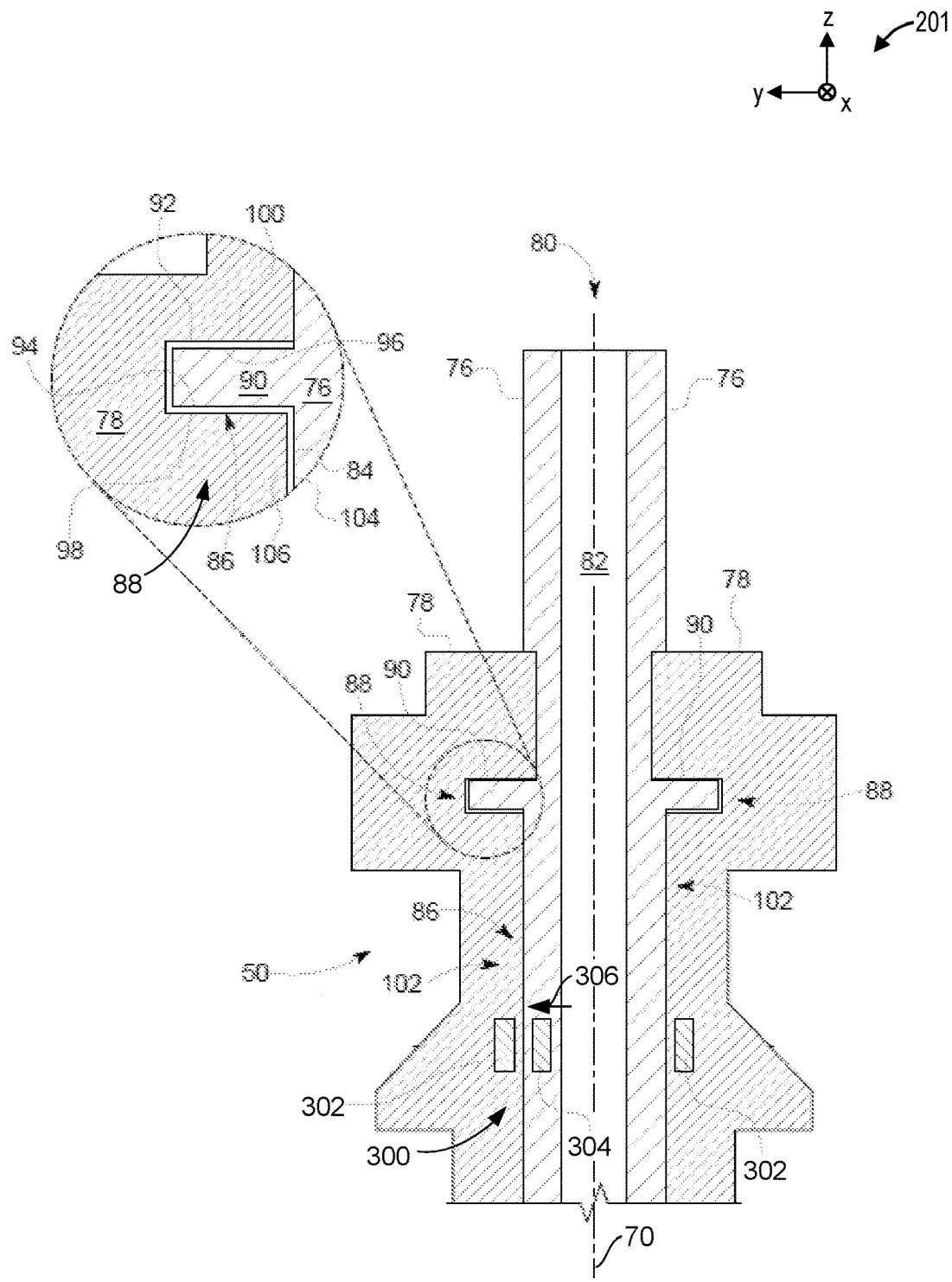
FIG. 3 shows a schematic view of a first example of a journal bearing for the x-ray tube of FIG. 2 with a gravitational load reducing mechanism.
Figure 4:
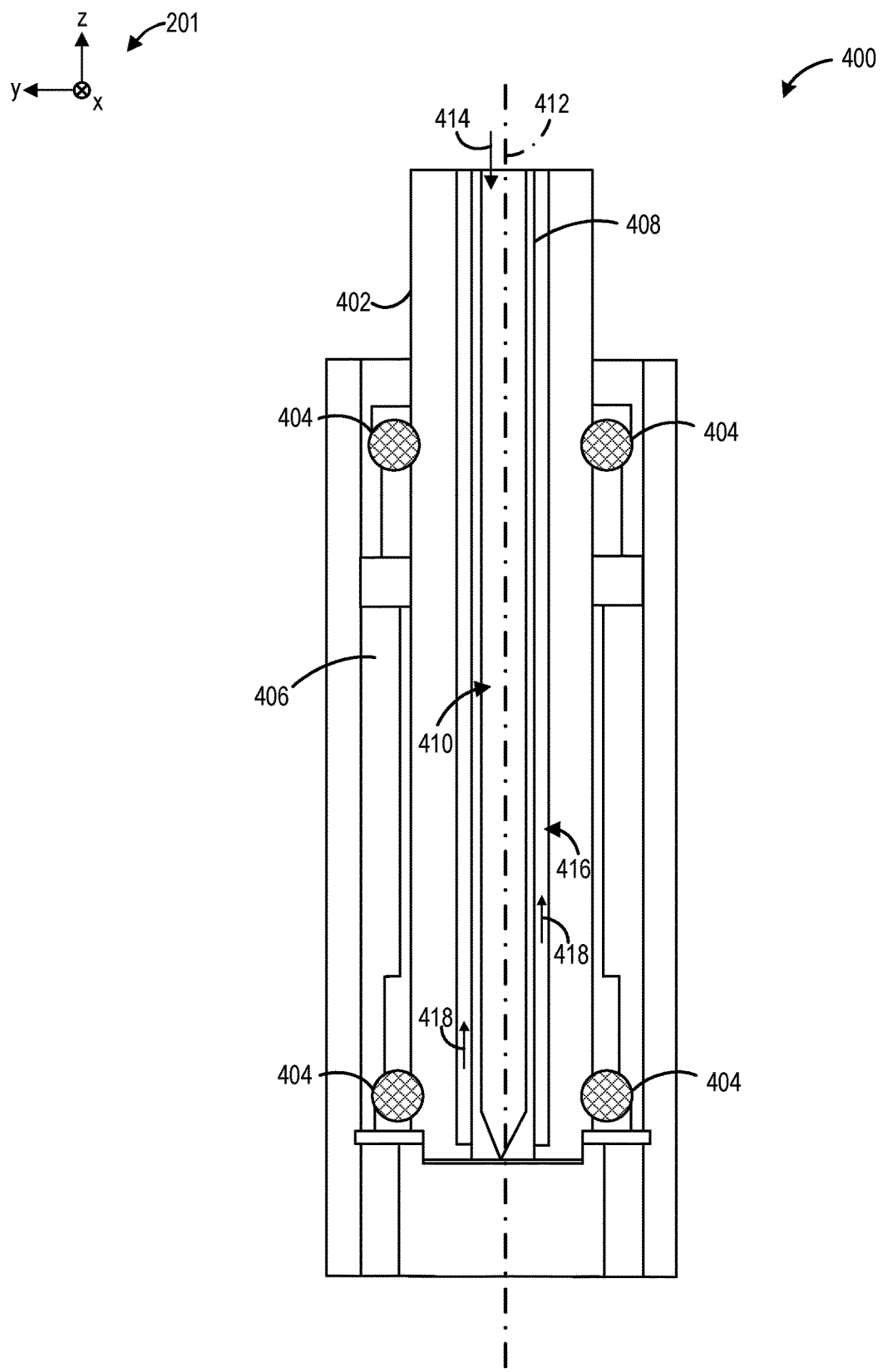
FIG. 4 shows a schematic view of a second example of a journal bearing of the x-ray tube of FIG. 2.
Figure 6:
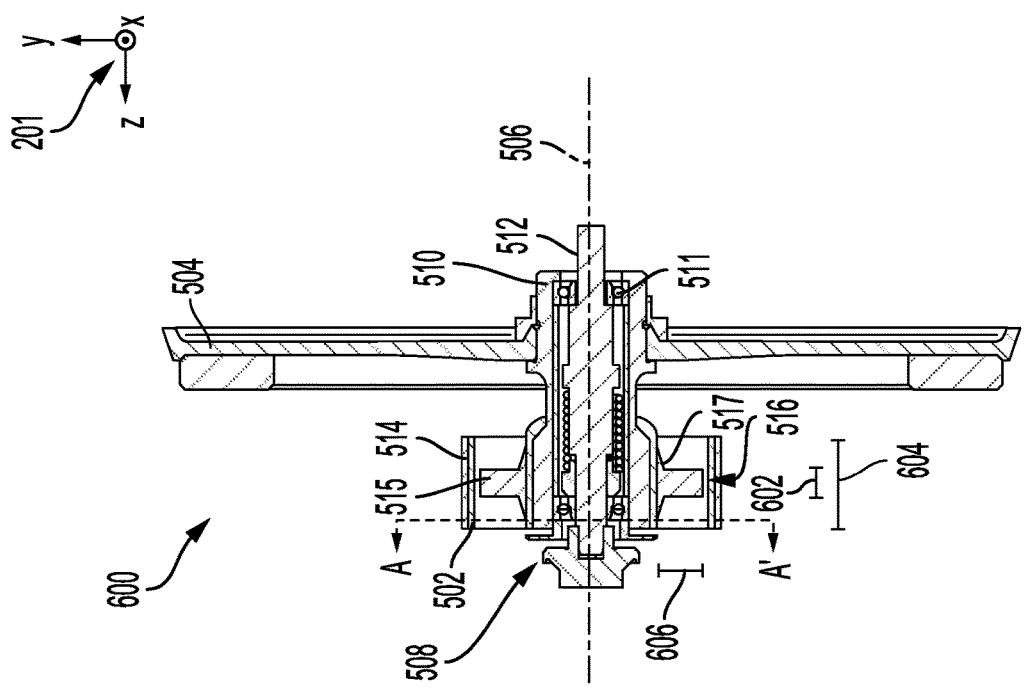
FIG. 6 shows a profile view of the first example of the rotor core of FIG. 5.
Figure 5:
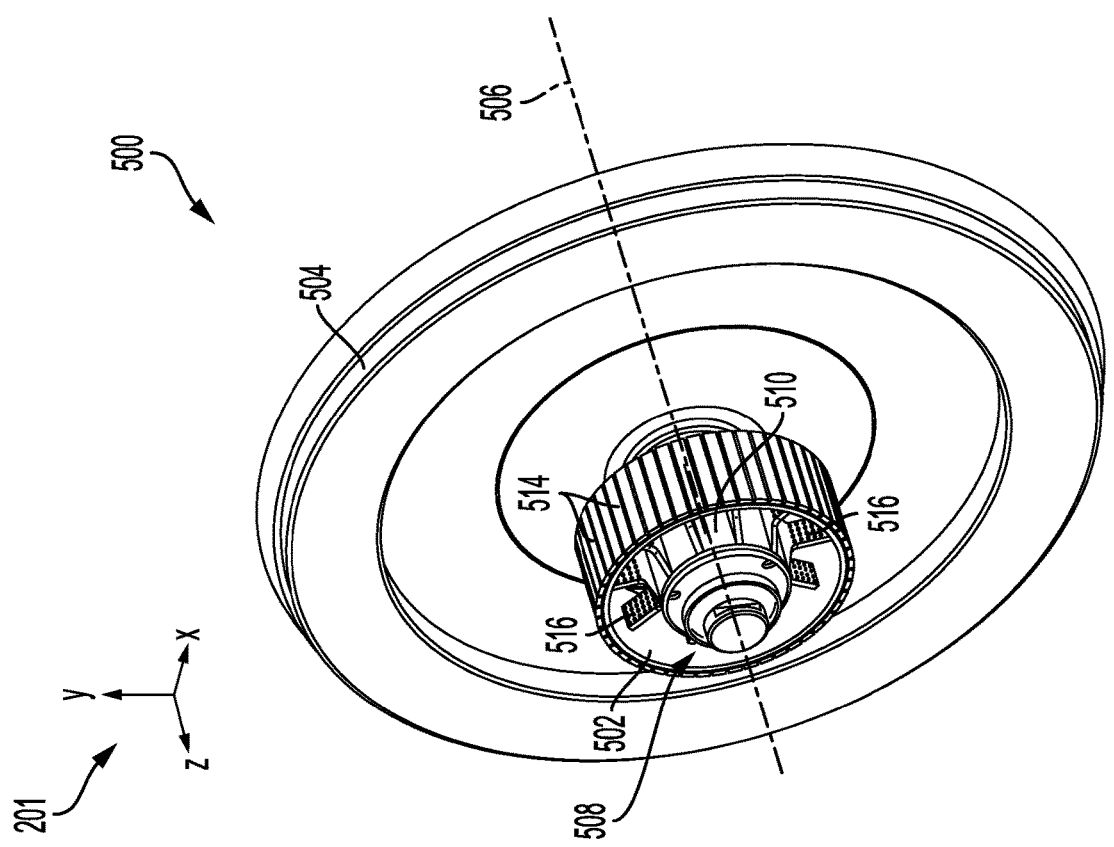
FIG. 5 shows a perspective view of a first example of a rotor core of a permanent magnet (PM) motor for an imaging system.
Figure 7:
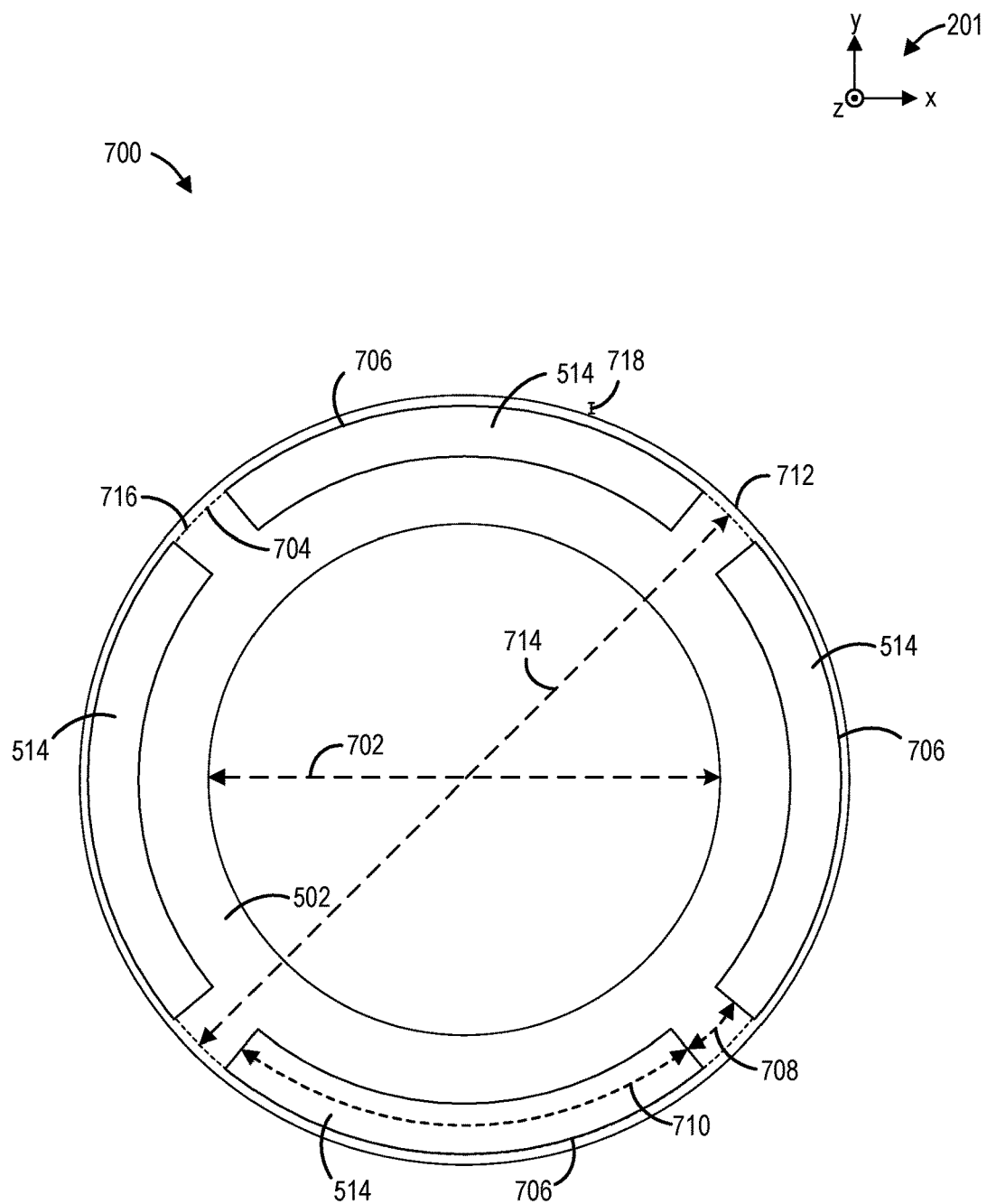
FIG. 7 shows a cross-section of the first example of the rotor core of FIGS. 5 and 6.
Figure 9:
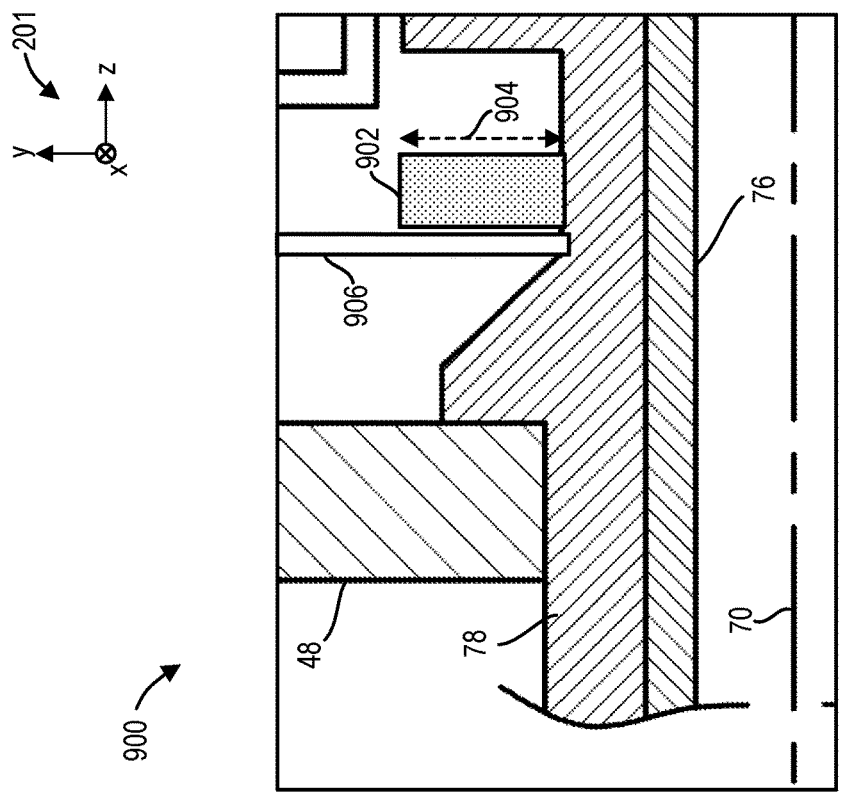
FIG. 9 shows a second example configuration of a magnet in a bearing assembly of the x-ray tube of FIG. 2.
Figure 8:
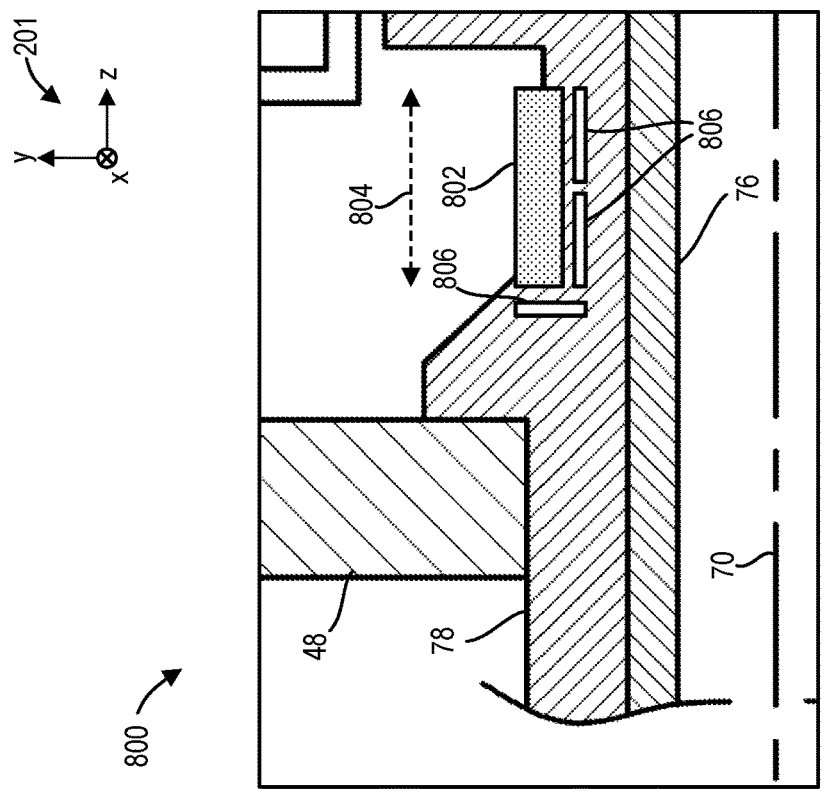
FIG. 8 shows a first example configuration of a magnet in a bearing assembly of the x-ray tube of FIG. 2.
Figure 12:
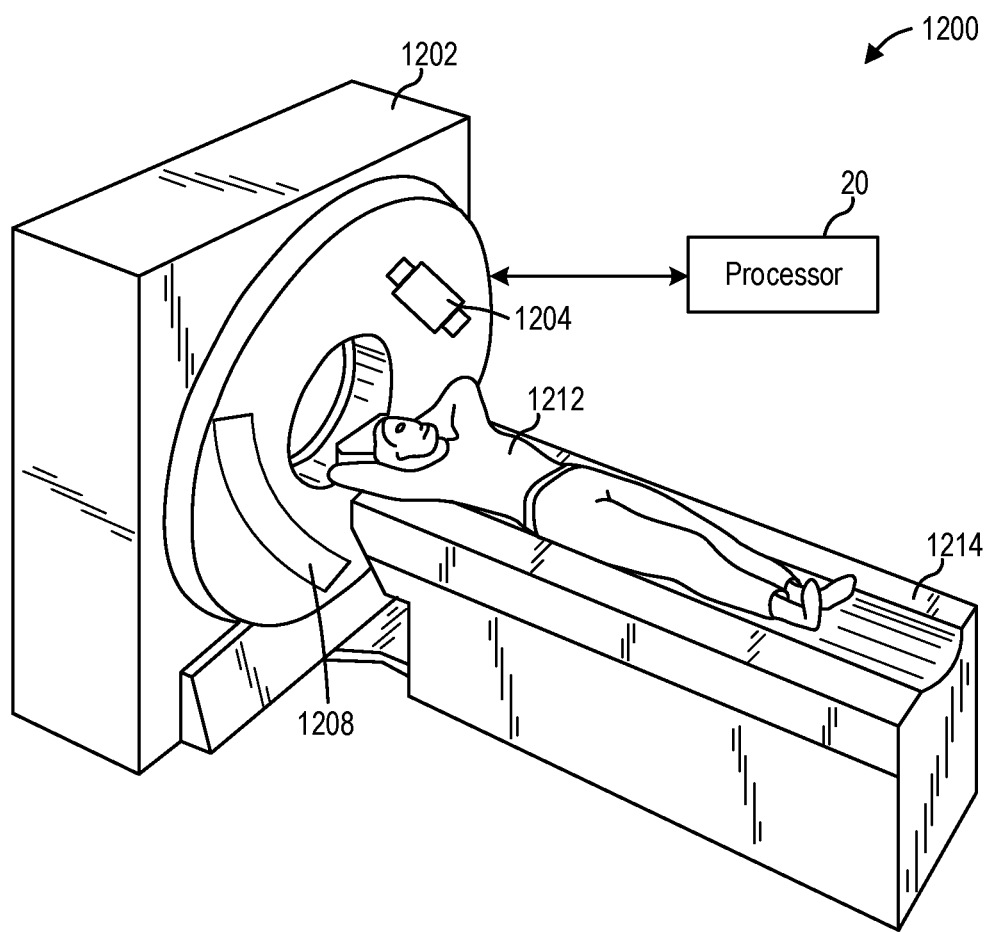
FIG. 12 shows a pictorial view of an exemplary embodiment of the imaging system of FIG. 1.

The following description relates to various embodiments of an x-ray tube for an imaging system. The x-ray tube may be included in an x-ray imaging system, an example of which is shown in FIG. 1. In one example, the x-ray imaging system may be a CT imaging, as shown in FIG. 12, which may include a rotating gantry. The x-ray imaging system includes an x-ray source or tube to generate irradiating x-ray beams. A cross-sectional view of the x-ray tube is shown in FIG. 2, the x-ray tube including a journal bearing, as illustrated in FIG. 3 in greater detail. The journal bearing of FIG. 3 may be configured as a liquid bearing assembly, including magnets positioned in a sleeve and a shaft of the bearing assembly. In another example, as shown in FIG. 4, the journal bearing may instead have a ball bearing assembly. Magnets may also be disposed in a rotor core of the PMSM, providing various benefits described further below. As such, the motor may be a permanent magnet synchronous motor (PMSM). Examples of the rotor core for the PMSM are illustrated in FIGS. 5-7 and 10. In some instances, as illustrated in FIGS. 5 and 6, the rotor core may include thermal barriers to inhibit heating of the magnets in the rotor core. Thermal barriers may also be included in the sleeve of the liquid metal bearing assembly, to block heating of the magnets in the sleeve by an x-ray target, as depicted in FIGS. 8 and 9.

Figure 13:
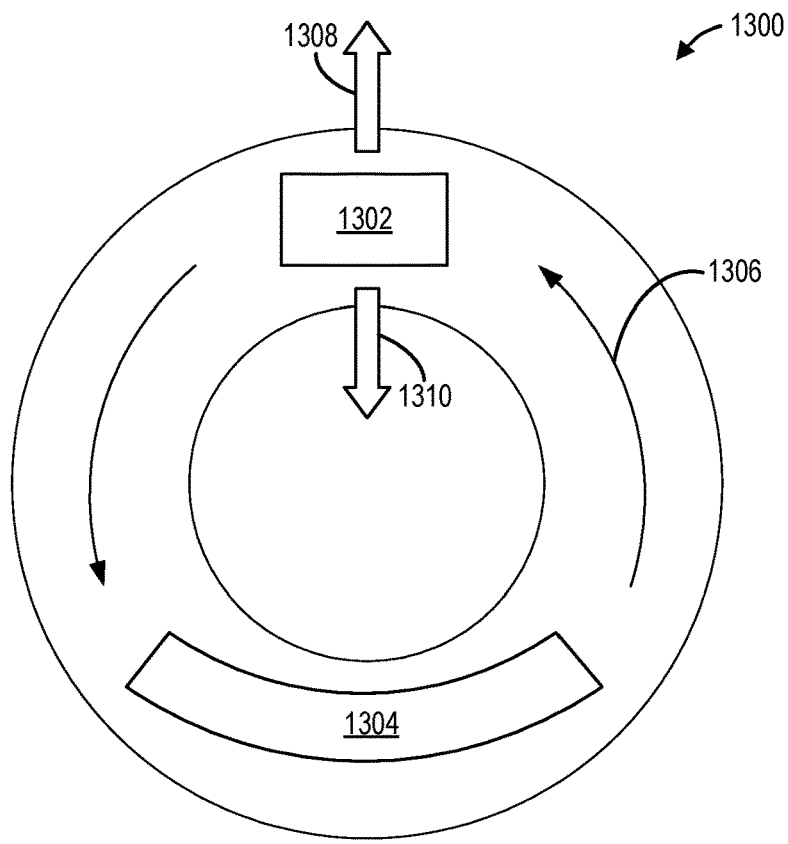
FIG. 13 shows an example of a gantry of a CT imaging system with an x-ray source in a first position.
Figure 14:
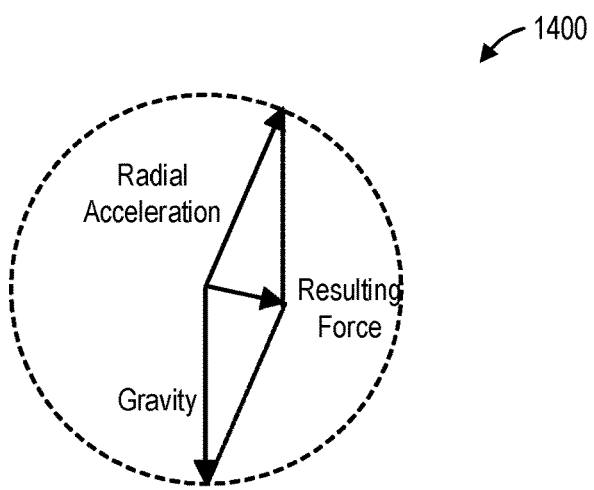
FIG. 14 shows a diagram of forces exerted on a rotor in the gantry of the CT imaging system.
Figure 15:
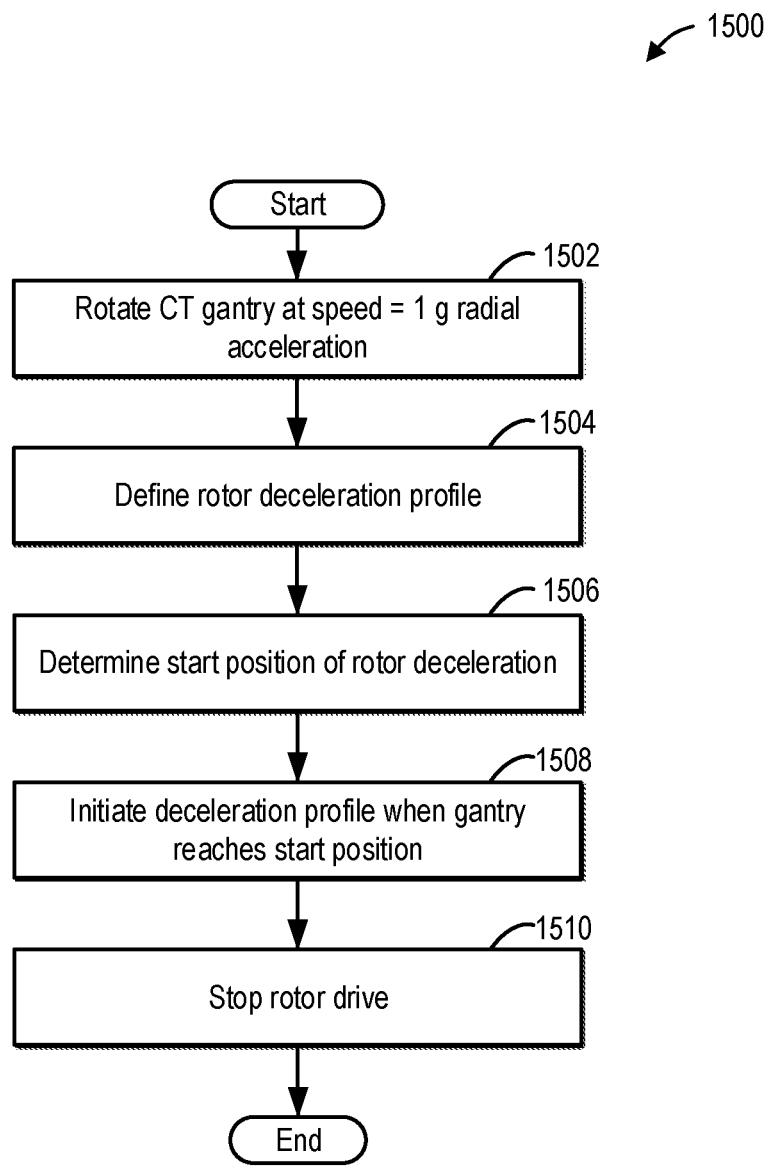
FIG. 15 shows an example of a method for controlling deceleration of a rotor in a CT imaging system enabled by monitoring of rotor speed.
Figure 16:
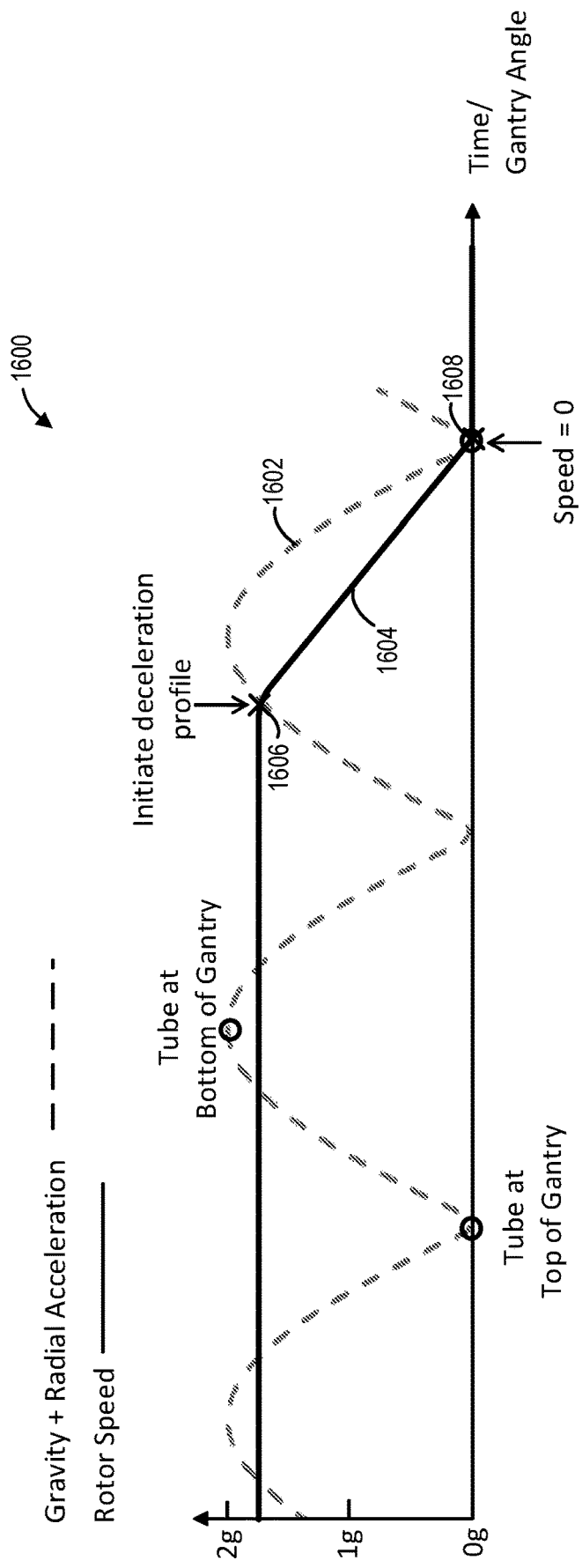
FIG. 16 shows a first graph plotting forces exerted on the rotor relative to time/gantry angle.

By arranging permanent magnets in the rotor core, or adapting the rotor with sensors and devices to measure speed and infer a position of the rotor, a deceleration profile of the rotor may be controlled to minimize abrasive contact between the sleeve and shaft of the journal bearing, when the journal bearing includes the liquid bearing assembly, during a window of reduced speed during which gravitational forces may overcome centrifugal forces that maintain the sleeve and shaft in non-rubbing contact at higher speeds. The window of reduced speed may coincide with the x-ray tube being in a first position, as shown in FIG. 13, where a gravitational force is offset by a radial acceleration when the x-ray tube is used in a CT imaging system. A diagram depicting a force applied to the rotor during rotation in the gantry, resulting from the gravitational force and the radial acceleration, is shown in FIG. 14. An example of a method for controlling the deceleration profile of the rotor, based on accurate monitoring of rotor speed and position and synchronizing gantry position with rotor speed is shown in FIG. 15 and a graph depicting the synchronizing of gantry position with rotor speed is depicted in FIG. 16. In addition to controlling the deceleration profile, knowledge of the rotor speed and position may be leveraged to perform various operations, including correcting for imperfections in the target, assessing high voltage instability events, treating defects in the target, as well as enabling focal spot wobble, z-wobble and fast kV applications. Example embodiments of the target and examples of methods of performing the aforementioned operations are provided in FIGS. 17-28.

FIGS. 2-12, 17, 20, 23, and 26-28 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

An x-ray tube of an imaging system may include a rotor enclosed within a vacuum chamber and a stator positioned external to the vacuum chamber, surrounding the rotor. An airgap may be present between the stator and rotor. In some examples, the airgap may be sufficiently large to adversely affect power transfer between the stator and rotor. Conventional induction motors demand rotor flux to be created through the stator current which, depending on the airgap and operating point, may result in utilization of a large portion of the stator current for magnetizing the rotor. This may lead to losses in the stator winding and increase an input current and power demand. In addition, control electronics used to power the motor may be enlarged to handle higher current levels.

In one example, by implementing a permanent magnet synchronous motor (PMSM) in the x-ray tube as an alternative to an induction motor, the input current demand may be reduced, as well as decreasing stator and electronic losses and cooling demands. The PMSM may have a higher power density, allowing a footprint of the motor to be reduced by decreasing a length of a rotor of the PMSM, the shortened rotor providing faster boost and higher torque production. Furthermore, rotor losses may be decreased in the PMSM, thereby minimizing rotor contributions to heat generation in the x-ray tube during operation. A shielded cable may be omitted which may otherwise lead to increased cost, ground leakage current, electromagnetic compatibility issues, etc. Electronics providing rotation control may be located on a housing of the x-ray tube or within close proximity to the x-ray tube rather than in a generator.

In addition, adapting the motor with permanent magnets may allow the motor to be implemented with lower voltage demands which may eliminate regulatory issues regarding clearance and creepage. A voltage of a rotation controller may also be reduced, removing demands for isolation. Increasing motor efficiency may also reduce cooling demands, thereby prolonging a useful life of the x-ray tube and reducing maintenance and repair. The PMSM may be fabricated via additive manufacturing which may preclude complex copper casting and machining used to produce conventional induction motors. As well, the rotor core may be manufactured as an integrated structure with a bearing sleeve and configured with Halbach array magnets when the rotor core is non-magnetic. A number of individually fabricated components may therefore be reduced. Further details of the PMSM are provided below with reference to FIGS. 5-10.

Additionally, the PMSM may allow precise monitoring of a speed and position of the rotor. The PMSM may operate at a supplied frequency and thus speed does not vary with load torque. As such, a speed of the motor is known via sensorless control, allowing efficient operating point determination, e.g., a minimum current to meet a torque demand, and ability to operate precisely at a desired speed. A phase, e.g., exact rotor position, may be inferred from electrical parameters of the electric drive. Thus the speed and position of the rotor may be monitored without relying on additional speed and position measurement devices.

Knowledge of the speed and position may also provide various advantages with regards to operating the imaging system with greater workflow efficiency and lower costs. It will be appreciated that while the PMSM is provided as one example of a motor for an imaging system that may provide the benefits described below without incorporating additional devices, similar effects may be obtained using other types of motors, such as the induction motor described with reference to the rotor core of FIG. 11. For example, the methods and processes described herein may be similarly applied to any other type of motor adapted with mechanisms for monitoring speed and position of the rotor, and thereby of a target coupled to the rotor. As an example, an induction motor configured with speed and position sensors may provide similar benefits. Further details of the methods are provided below, with reference to FIGS. 13-28.

Turning now to FIG. 1, a block diagram is shown of an embodiment of an imaging system 10 configured both to acquire original image data and to process the image data for display and/or analysis in accordance with exemplary embodiments. It will be appreciated that various embodiments are applicable to numerous medical imaging systems implementing an x-ray tube, such as x-ray or mammography systems. Other imaging systems such as computed tomography (CT) systems and digital radiography (RAD) systems, which acquire image three dimensional data for a volume, also benefit from the present disclosure. The following discussion of imaging system 10 is merely an example of one such implementation and is not intended to be limiting in terms of modality.

As shown in FIG. 1, imaging system 10 includes an x-ray tube or source 12 configured to project a beam of x-rays 14 through an object 16. Object 16 may include a human subject, pieces of baggage, or other objects desired to be scanned. X-ray source 12 may be conventional x-ray tubes producing x-rays 14 having a spectrum of energies that range, typically, from thirty (30) keV to two hundred (200) keV. The x-rays 14 pass through object 16 and, after being attenuated, impinge upon a detector assembly 18. Each detector module in detector assembly 18 produces an analog electrical signal that represents the intensity of an impinging x-ray beam, and hence the attenuated beam, as it passes through the object 16. In one embodiment, detector assembly 18 is a scintillation based detector assembly, however, it is also envisioned that direct-conversion type detectors (e.g., CZT detectors, etc.) may also be implemented.

A processor 20 receives the signals from the detector assembly 18 and generates an image corresponding to the object 16 being scanned. A computer 22 communicates with processor 20 to enable an operator, using operator console 24, to control the scanning parameters and to view the generated image. That is, operator console 24 includes some form of operator interface, such as a keyboard, mouse, voice activated controller, or any other suitable input apparatus that allows an operator to control the imaging system 10 and view the reconstructed image or other data from computer 22 on a display unit 26. Additionally, console 24 allows an operator to store the generated image in a storage device 28 which may include hard drives, floppy discs, compact discs, etc. The operator may also use console 24 to provide commands and instructions to computer 22 for controlling a source controller 30 that provides power and timing signals to x-ray source 12.

In one example, the imaging system 10 of FIG. 1 may be configured as a CT system 1200 for CT imaging, an example of which is depicted in FIG. 12. Particularly, the CT system 1200 is configured to image a subject 1212 such as a patient, an inanimate object, one or more manufactured parts, and/or foreign objects such as dental implants, stents, and/or contrast agents present within the body. In one embodiment, the CT system 1200 includes a gantry 1202, which in turn, may further include at least one x-ray source 1204 configured to project a beam of x-ray radiation (e.g., the x-rays 14 of FIG. 1) for use in imaging the subject 1212 laying on a table 1214. Specifically, the x-ray source 1204 is configured to project the x-ray radiation beams towards a detector array 1208 positioned on the opposite side of the gantry 1202. Although FIG. 12 depicts only a single x-ray source 1204, in certain embodiments, multiple x-ray sources and detectors may be employed to project a plurality of x-ray radiation beams for acquiring projection data at different energy levels corresponding to the patient. In some embodiments, the x-ray source 1204 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 1200 further includes the image processor 20 configured to reconstruct images of a target volume of the subject 1212 using an iterative or analytic image reconstruction method. For example, the image processor 20 may use an analytic image reconstruction approach such as filtered back projection (FBP) to reconstruct images of a target volume of the patient. As another example, the processor 20 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 1212. As described further herein, in some examples the processor 20 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of a radiation beam by the object. Each detector element of the array produces a separate electrical signal that is a measurement of the x-ray beam attenuation at the detector location. The attenuation measurements from all the detector elements are acquired separately to produce a transmission profile.

FIG. 2 illustrates a cross-sectional view of an x-ray source 200 which may be included in the imaging system of FIG. 1 and the CT system 1200 of FIG. 12. For example, the x-ray source 200 may be an exemplary embodiment of the x-ray source 12 of FIG. 1 and 1204 of FIG. 12, formed of an x-ray tube 40 that includes an anode assembly 42 and a cathode assembly 44. A set of reference axes 201 are provided for comparison between views shown, indicating an x-axis, a y-axis, and a z-axis. X-ray tube 40 is supported by the anode and cathode assemblies 42, 44 within an envelope or frame 46, which houses a target or anode 48, a bearing assembly 50, and a cathode 52. Frame 46 defines an area of relatively low pressure (e.g., a vacuum) compared to ambient, in which high voltages may be present. Frame 46 may be positioned within a casing (not shown) filled with a cooling medium, such as oil, that may also provide high voltage insulation. While the target and anode are described above as being a common component of x-ray tube 40, the target and anode may be separate components in alternative x-ray tube embodiments.

In operation, an electron beam 54 is produced by cathode assembly 44. In particular, cathode 52 receives one or more electrical signals via a series of electrical leads 56. The electrical signals may be timing/control signals that cause cathode 52 to emit electron beam 54 at one or more energies and at one or more frequencies. The electrical signals may also at least partially control the potential between cathode 52 and anode 48. Cathode 52 includes a central insulating shell 58 from which a mask 60 extends. Mask 60 encloses electrical leads 56, which extend to a cathode cup 62 mounted at the end of mask 60. In some embodiments, cathode cup 62 serves as an electrostatic lens that focuses electrons emitted from a thermionic filament within cathode cup 62 to form electron beam 54.

X-rays 64 are produced when high-speed electrons of electron beam 54 are suddenly decelerated when directed from the cathode 52 to a target or focal surface 66 formed on target 48 via a potential difference therebetween of, for example, sixty (60) thousand volts or more in the case of CT applications. The x-rays 64 are emitted through a radiation emission passage 68 formed in frame 46 toward a detector array, such as detector assembly 18 of FIG. 1 and detector array 1208 of FIG. 12.

Anode assembly 42 includes a rotor 72 and a stator (not shown) located outside x-ray tube 40 and surrounding rotor 72 for causing rotation of anode 48 during operation. Target 48 is supported in rotation by a bearing assembly 50, which, when rotated, also causes target 48 to rotate about the centerline 70. As shown, target 48 has an annular shape, which contains a circular opening 74 in the center thereof for receiving bearing assembly 50.

Target 48 may be manufactured to include a number of metals or alloys, such as tungsten, molybdenum, copper, or any material that contributes to bremsstrahlung (i.e., deceleration radiation) when bombarded with electrodes. Target or focal surface 66 of target 48 may be selected to have a relatively high refractory value so as to withstand the heat generated by electrons impacting target 48. Further, the space between cathode assembly 44 and target 48 may be evacuated in order to minimize electron collisions with other atoms and to maximize an electric potential.

To avoid overheating of the target 48 when bombarded by the electrons, rotor 72 rotates target 48 at a high rate of speed (e.g., 90 to 250 Hz) about a centerline 70. In addition to the rotation of target 48 within frame 46, in a CT application, the x-ray tube 40 as a whole is caused to rotate about an object, such as object 16 of imaging system 10 in FIG. 1, at rates of typically 1 Hz or faster.

Bearing assembly 50 can be formed as necessary, such as with a number of suitable ball bearings (as shown in FIG. 4), but in the illustrated exemplary embodiment comprises a liquid metal hydrodynamic bearing having adequate load-bearing capability and acceptable acoustic noise levels for operation within imaging system 10 of FIG. 1.

In general, bearing assembly 50 includes a stationary component, such as center shaft 76, and a rotating portion, such as sleeve 78 to which the target 48 is attached. While center shaft 76 is described with respect to FIG. 2 as the stationary component of bearing assembly 50 and sleeve 78 is described as the rotating component of bearing assembly 50, embodiments of the present disclosure are also applicable to embodiments wherein center shaft 76 is a rotary shaft and sleeve 78 is a stationary component. In such a configuration, target 48 would rotate as center shaft 76 rotates.

Center shaft 76 may optionally include a cavity or coolant flow path 80 though which a coolant 82 (as shown in FIG. 3), such as oil, may flow to cool bearing assembly 50. As such, coolant 82 enables heat generated from target 48 of x-ray tube 40 (as shown in FIG. 2) to be extracted therefrom and transferred external from x-ray tube 40. In straddle mounted x-ray tube configurations, coolant flow path 80 extends along a longitudinal length of x-ray tube 40, e.g., along the centerline 70. In alternative embodiments, coolant flow path 80 may extend through only a portion of x-ray tube 40, such as in configurations where x-ray tube 40 is cantilevered when placed in an imaging system.

Referring now to FIG. 3, a cross-sectional view of a portion of bearing assembly 50 is shown according to an embodiment. It will be noted that FIG. 3 is oriented perpendicular relative to FIG. 2 for illustrative purposes but may be positioned within the vacuum chamber as shown in FIG. 2. Bearing assembly 50 includes a center shaft 76 positioned within sleeve 78, which is configured to support an anode (not shown), such as target 48 of FIG. 2. A lubricant 84 is positioned in a gap 86 formed between center shaft 76 and sleeve 78. In some examples, lubricant 84 is a metal or metallic alloy that exists in a liquid state at an operating temperature of bearing assembly 50, where bearing assembly 50 is a liquid metal bearing assembly.

The lubricating fluid 84 flowing between the rotating and stationary components of the bearing assembly 50 may include a variety of individual fluids as well as mixtures of fluids. For example, multiple liquid metals and liquid metal alloys may be used as the lubricating fluid, such as an indium gallium alloy. More generally, fluids with relatively low vapor pressures that are resistant to evaporation in vacuum-level pressures of the x-ray tube may be used. In the present context, low vapor pressures may generally be in the range of $1\times10^{-5}$ Torr. In other words, fluids that are stable in vacuums are desirable for use in x-ray tube systems so as to not adversely affect the established vacuum during operation of the system. In the present disclosure, lubricant 84 may be gallium or a gallium alloy as non-limiting examples.

Exemplary base materials of center shaft 76 and sleeve 78 of bearing assembly 50 include ceramics, metals, and combinations thereof. In one embodiment, center shaft 76 and sleeve 78 are constructed of the same base material. Alternatively, the base materials of center shaft 76 and sleeve 78 may differ.

In the embodiment illustrated in FIG. 3, center shaft 76 of bearing assembly 50 is a stationary component and sleeve 78 is a rotatable component constructed to rotate about center shaft 76. However, the example shown in FIG. 3 is non-limiting and alternative bearing configurations have been contemplated. As one example, bearing assembly 50 may instead include a stationary outer component and a rotating center shaft having a target attached thereto. As another example, bearing assembly 50 may be a "straddle" bearing that is configured to support a target between a first and a second liquid metal bearing. In other words, embodiments of the bearing assembly may be incorporated into any bearing configuration utilizing a liquid lubricated bearing to support an anode or target. Such configurations may include a stationary center shaft and a rotatable outer shaft, and vice versa. Furthermore, such applications may not be limited to x-ray tubes, but may be applied to any configuration having a rotating component in a vacuum, the rotating component being supported by a liquid lubricated bearing. Thus, aspects of the present disclosure are applicable to any bearing configuration having a rotatable component and a stationary component, and a liquid lubricant therebetween, regardless of configuration or application.

As illustrated in FIG. 3, center shaft 76 of bearing assembly 50 includes a thrust bearing portion 88 comprising a radial projection 90 that extends from center shaft 76 and is positioned in a radial cavity 92 of sleeve 78. Radial projection 90 of thrust bearing portion 88 includes a pair of outer bearing surfaces 94, 96 that face inner bearing surfaces 98, 100 of sleeve 78. In cantilever mount embodiments, sleeve 78 may also include a removable endcap (not shown) to allow assembly of components. Radial projection 90 inhibits axial motion of sleeve 78 relative to center shaft 76, and, as illustrated, lubricant 84 is also included between radial projection 90 and sleeve 78. Radial projection 90 need not be limited in axial length, but may be extended in axial length to provide additional mechanical support of components.

A radial or journal bearing portion 102 of bearing assembly 50 is located adjacent thrust bearing portion 88. An inner surface 104 of journal bearing portion 102 of center shaft 76 faces an outer surface 106 of journal bearing portion 102 of sleeve 78. While journal bearing portion 102 is illustrated on a first side of thrust bearing portion 88 adjacent outer race surface 94, other examples of the bearing assembly 50 may include a second journal bearing portion located on a second side of thrust bearing portion 88 adjacent inner race surface 96. Various coatings, textures, and patterns including grooves embedded in the contacting surfaces of bearing assembly 50 may be applied to alter bearing behavior as the shaft 76 and sleeve 78 rotate relative to each other.

Bearing assembly 50 may be referred to as a spiral groove bearing (SGB) due to the patterning of grooves along the various surfaces of the bearing. In some examples, the spiral groove may be formed from a logarithmic spiral shape. The spiral groove bearing may also be equivalently referred to as a hydrodynamic bearing or liquid bearing. In such spiral groove bearings, ways to contain the liquid lubricant 84 may be categorized in two general methods. The first includes providing physical barriers near the ends of the bearing where shaft seals would be placed in other applications. Rubber or other types of shaft seals in the presence of the vacuum inside the x-ray tube may function improperly, degrade quickly, and/or destroy the pressure inside the x-ray tube. For similar reasons, o-rings, grease, or other conventional means for aiding in rotational lubrication between two components may be undesirable because of the vacuum in the x-ray lube. Greases and other lubricants with lower vapor pressure than liquid metals may vaporize and destroy the vacuum. In some examples, physical walls of different shapes and sizes may be placed at different angles to capture the lubricant to reduce leakage through the bearing.

The second general method includes utilizing the capillary forces of the lubricant, wherein the small gap between two opposing bearing surfaces wets the fluid to retain the fluid within the gap. In other words, the anti-wetting properties of the surface (via texturing, coating, or both) aids in preventing the lubricant from flowing in between the small gaps. In some examples, the surfaces are coated and/or textured to be more wetted such that the lubricant clings via adhesion in the small gap to reduce lubricant moving through the gap. In other examples, the surfaces are coated and/or textured to be more anti-wetting such that the lubricant is pushed away from the small gaps near the ends of the bearing assembly. In this context, the small gap may be in the range of 50 microns.

Operation of liquid bearings in x-ray tube systems, such as bearing assembly 50 of FIGS. 2 and 3, may be at least partially dependent on a tradeoff between load carrying capacity and fluid pumping force. In some examples, the load carrying capacity and fluid pumping force are inversely proportional and directly related to a geometry of the bearing grooves. For example, given a substantially constant rotational speed of the liquid bearing, deeper grooves may provide a higher pumping force, while the increased clearance between the shaft and sleeve can reduce the load carrying ability of the bearing. Pumping force may be utilized to contain the lubrication fluid and anti-wetting coatings may be applied to sealing surfaces to further assist in containing the lubrication fluid.

Due to the relative motion of the sleeve and shaft, the lubricating fluid is moved in a number of ways, including but not limited to, shearing, wedging, and squeezing, thereby creating pressures to lift and separate the shaft and sleeve from each other. This effect enables the liquid bearing to function and provide low-friction movement between the shaft and sleeve. In other words, shearing of the lubricating fluid imparts energy into the fluid which causes the fluid to pump, wherein the pumping action into the gap between the shaft and sleeve is how the liquid bearing functions. Energy transfer from the surfaces to the fluid enables bearing functionality. In application, in the context of the x-ray tube, wetting between some bearing surfaces and the lubricating fluid allows shearing to impact energy to the fluid. However, anti-wetting between some bearing surfaces and the lubricating fluid allows friction between the bearing surfaces to be reduced, thereby reducing operating temperatures of the bearing assembly.

As another example, as shown FIG. 4, a bearing assembly 400 may be a ball bearing assembly instead of a liquid metal bearing assembly, similarly arranged in an x-ray source such as the x-ray source 200 of FIG. 2. The bearing assembly 400 has a cylindrically hollow bearing housing 402. Ball bearings 404 are positioned in contact with an outer surface of the bearing housing 402, and nested in, for example, races disposed in the outer surface of the bearing housing 402. The ball bearings 404 may also be in contact with races in an inner surface of a rotor core 406. The ball bearings 404 may be rigid metal balls formed of a material such as high speed steel coated with lead or silver lubricant. However, other materials may also be used.

The bearing housing 402 encloses an inner cooling shaft 408 with a central bore 410 centered about a central axis 412 of the bearing assembly 400. A coolant, such as oil, may flow through the central bore 410 as indicated by arrow 414 and continue through an oil return path 416 surrounding the inner cooling shaft 408, as indicated by arrows 418. The coolant may provide cooling to the ball bearings 404 as rotation of the rotor core 406 drives rotation of the bearing housing 402, in contact with the ball bearings 404. The rotor core 406 may be coupled to an anode of the x-ray source, e.g., the anode 48 of FIG. 2, and thereby also drive rotation of the anode. The ball bearings 404 may ensure that the rotor core 406 rotates smoothly and with minimal frictional resistance around the bearing housing 402 and the central axis 412.

It will be appreciated that the bearing assemblies shown in FIGS. 3 and 4 are non-limiting examples. Other examples may include bearing assemblies with different geometries, relative sizes of components, positioning of components, level of complexity, etc. In another example, the liquid metal bearing assembly and ball bearing assembly may be combined within a single x-ray source.

Returning to FIG. 3, some examples of bearing assembly 50 may include a load reduction mechanism/magnetic bearing assembly 300 when the bearing assembly 50 is a liquid bearing assembly. The load reduction mechanism 300 may include magnets 302 located on or within the material forming the sleeve 78 at one or more specified portions of the sleeve 78. These portions generally correspond to the locations where the shaft 76 is known to most frequently rub against the sleeve 78 when fluid pressure from the lubricant 84 is insufficient to overcome the force of gravity acting on the sleeve 78 relative to the shaft 76. The magnets 302 may be located within the sleeve 78 around the circumference of the sleeve 78 in order to provide a magnetic force at each point around the sleeve 78 at the specified portion(s). In an alternative exemplary embodiment, while the magnets 302 may be discrete magnetic elements with each magnetic element located at one of the specified portions, the load reduction mechanism 300 may instead have a single annular magnet disposed on or within the sleeve 78 and configured to have equivalent properties and same effect as the individual magnets 302.

To interact with the magnets 302 in the sleeve 78, the bearing assembly 50 includes a separate positioning magnet(s) 304 disposed adjacent to an in alignment with one of the magnets 302 of the sleeve 78. The positioning magnet 304 may be disposed at any suitable location relative to the magnet 302 such that a magnetic field generated by the positioning magnet 304 may interact with the magnetic field created by each of the magnets 302 disposed within the sleeve 78.

The magnets, e.g., the magnets 302 in the sleeve 78 and the positioning magnets 304, may be permanent magnets (passive) or electromagnets (active) that act with repulsive or attractive force toward each other. These forces help the sleeve 78 to be centered around the shaft 76 to provide a net force which counteracts or reduces the gravitational force of the rotating components at 1 g, thereby preventing rubbing of the shaft 76 and sleeve 78 against one another at low rotational speeds where the pressure of the lubricant 84 is insufficient to provide the necessary force on the sleeve 78 to maintain the desired clearance or tolerance for the gap 86, which in one example may be between 20 µm and 100 µm.

In the exemplary embodiment of FIG. 3, the positioning magnet 304 is disposed within the shaft 76 such that the magnetic forces generated by the magnets 302 and the positioning magnet 304 operate to provide a force on the sleeve 78 in the direction of arrow 306 in FIG. 3 as a result of the repulsive force exerted between the magnets 302 and the positioning magnet 304. Due to the placement of the magnets 302 around the entire circumference of the sleeve 78, this repulsive force continually acts on the sleeve 78 as it rotates around the shaft 76, which at low speeds this mitigates rubbing between the shaft 76 and the sleeve 78.

Additionally, magnets may be disposed in a rotor of an x-ray tube. In such instances, the x-ray tube may be configured with a PMSM and the magnets in the rotor may be permanent magnets. An example of a portion of a PMSM with permanent magnets located in a rotor core of the motor is shown from a perspective view 500 in FIG. 5 and a profile view 600 in FIG. 6. A rotor core 502 of the PMSM is linked to a target 504. The rotor core 502 and target 504 have a common central axis 506.

The rotor core 502 may be linked to the target 504 by a bearing assembly 508, similar to the bearing assembly 50 of FIGS. 2 and 3 or the bearing assembly 400 of FIG. 4, including a sleeve 510 and a center shaft 512, as shown in FIG. 6. The bearing assembly 508 is adapted with ball bearings 511 in FIG. 6 but may be instead be configured with liquid bearings, in other examples. Furthermore, the sleeve 510 may be a SGB sleeve. The sleeve 510 of the bearing assembly 508 is circumferentially surrounded by the rotor core 502 along a first portion of the sleeve 510 and circumferentially surrounded by the target 504 at a second portion of the sleeve 510, the first and second portions adjacent to one another along the z-axis.

The rotor core 502 may have magnets 514 disposed along an outer surface of the rotor core 502 and covering the entire outer surface of the rotor core 502. The magnets 514 may each have rectangular geometries and be arranged in edge-sharing contact with adjacent magnets 514 or spaced away from adjacent magnets 514. In one example, the magnets 514 may be permanent magnets formed from, for example, samarium cobalt with operating heat tolerances of up to 550° C. In other examples, the magnets 514 may be formed from another material such as neodymium boron iron or other magnetic materials with heat tolerances above an operating temperature of the x-ray tube.

The rotor core 502 may be magnetic or non-magnetic and may be additively manufactured with a sleeve of a bearing assembly as a continuous unit. Magnetic powders for 3D printing may also be used, such as 1018 steel and iron cobalt alloy, to form the magnetic rotor core 502. When the rotor core 502 is configured to be non-magnetic, the rotor core 502 may be formed of a non-magnetic material such as cobalt chromium molybdenum, molybdenum, deuterated tool steel, or any other non-magnetic material compatible with gallium (e.g., gallium used in liquid metal bearings of the bearing assembly 508) which may enable the rotor core 502 to be integrated with the sleeve 510 of the bearing assembly 508.

For example, the non-magnetic rotor core 502 and the sleeve 510 may be formed as a single, continuous unit, e.g., integrated, and fabricated by, for example, additive manufacturing. As one example, the rotor core 502 and the sleeve 510 may be 3D printed together thus reducing a number of individually fabricated components of the x-ray tube. The non-magnetic rotor core 502 may be equipped with the Halbach array magnets which form a strong magnetic field on one side of the magnet array. For example, the magnets 514 may each be a segmented magnet of the Halbach array, each magnet magnetized in a different direction to approximate a sinusoidal field distribution in the air.

By implementing the Halbach array in the rotor core 502, a hysteresis loss is not present on the rotor core 502 and harmonic content and torque ripple are reduced, thereby reducing a demand for skewing. By forming the rotor core 502 from a non-magnetic material, an amount of material for the rotor core 502 is determined by integration and mechanical demands. Concentrated windings on a stator may be used, allowing a footprint of the stator to also be reduced.

The non-magnetic rotor core may also enable a retention sleeve to be integrated with the rotor core and bearing assembly sleeve. The retention sleeve may be a tubular structure configured to circumferentially surround the rotor core, as shown in FIG. 7 in a cross-section 700 of the rotor core. The cross-section 700 is taken along line A-A' indicated in FIG. 6. The bearing assembly 508 is omitted in FIG. 7 for brevity.

Cross-section 700 depicts a continuous circular geometry of the rotor core 502. The rotor core 502 may have an inner diameter 702 that may be determined by an outer diameter of the sleeve 510 of the bearing assembly 508, as shown in FIG. 6. In some examples, the inner diameter 702 of the rotor core 502 may be as large as may be accommodated in a vacuum chamber of the x-ray tube to reduce a length, and therefore a weight and inertia of the rotor core 502 when the rotor core 502 is formed of a non-magnetic material.

The magnets 514 may be arranged in the rotor core 502 along an outer surface 704 of the rotor core 502. For example, the magnets 514 may be embedded in the rotor core 502 so that outer surfaces 706 of the magnets are flush with the outer surface 704 of the rotor core 502, forming a smooth, continuous surface. In other examples, such as interior permanent magnet configurations, the magnets 514 may be embedded within an interior of the rotor core 502 such that the outer surfaces 706 of the magnets 514 are not exposed. The magnets 514 are shown spaced apart from one another by a distance 708 between ends of the magnets 514. The distance 708 may vary depending on a configuration of the magnets 514 in the rotor core 502. For example, an arc span 710 of the magnets 514 may be longer or shorter than shown in FIG. 7 based on torque ripple, losses, number of poles, manufacturing demands, etc., of a motor of the x-ray tube. Additionally, a number of magnets 514 embedded in the rotor core 502 may differ from that shown in FIG. 7 based on the arc span 710 of the magnets 514 and a desired spacing between the magnets 514. In some examples, the arc span 710 of the magnets 514 may not be uniform around the rotor core 502.

A retention sleeve 712 may circumferentially surround and enclose the rotor core 502. The retention sleeve 712 may have an inner diameter 714 that is similar to an outer diameter of the rotor core 502. As such, an inner surface 716 of the retention sleeve 712 may be in face-sharing contact with the outer surface 704 of the rotor core 502 as well as the outer surfaces 706 of the magnets 514. The retention sleeve 712 may maintain a position of the magnets 514 as the rotor core 502 rotates at high speed and a strong centrifugal force is imposed on the magnets 514. A thickness 718 of the retention sleeve 712 may vary based on mechanical properties of a material of the retention sleeve 712. The retention sleeve 712 may be formed from a similar material as the rotor core 502.

In one example, when the rotor core 502 is non-magnetic, the retention sleeve 712 may be formed of a same material as the rotor core 502 and the rotor core 502 and the retention sleeve 712 may be integrated as a single, continuous, united structure. The integrated retention sleeve 712 and rotor core 502 may be fabricated via additive manufacturing, thereby lowering manufacturing costs. The continuous structure may be printed, e.g., 3D printed, with slots for the magnets 514 which may be inserted into the slots after printing is complete.

In some examples, the rotor core 502, retention sleeve 712, and the sleeve 510 of the bearing assembly 508 (as shown in FIG. 6) may be additively manufactured together as a single continuous unit when the components (e.g., the rotor core 502, retention sleeve 712, and bearing assembly sleeve 510) are implemented in a PMSM. Manufacturing of the components is thereby simplified and costs further reduced. In instances where the components are implemented in an induction motor, the rotor core 502 may be additively manufactured to form an integrated unit with the bearing assembly sleeve 510. The integrated rotor core 502 and sleeve 510 may be formed of a magnetic material such as steel or molybdenum. The retention sleeve 712 may be omitted in the induction motor.

In addition to lowering costs and simplifying fabrication, additive manufacturing of the rotor core, with one or more of the retention sleeve and bearing assembly sleeve, may enable incorporation of one or more thermal barriers between the bearing assembly and the rotor core. The thermal barriers may provide a cooling effect that assists in maintaining a temperature of the magnets of the rotor core below a heat tolerance threshold of the magnets. Exposure of the magnets to temperatures above their tolerance threshold may lead to, for example, de-magnetization of the magnets.

Returning to FIGS. 5 and 6, thermal barriers 516 are shown extending radially between the sleeve 510 of the bearing assembly 508 and the rotor core 502. The thermal barriers 516 may be arranged similar to spokes of a wheel, forming planar structures evenly spaced apart around a circumference of the sleeve 510. As shown in FIG. 6, each of the thermal barriers 516 may have a first, rectangular portion 515, and a second, flared portion 517, the first and second portions 515, 517 continuous with one another. A width 602 of the first portion 515 of the thermal barriers 516 may be less than a width 604 of the rotor core 502, the widths defined along the z-axis. A width of the second portion 517 of the thermal barriers 516 may decrease from the width 604 of the rotor core 502 to the width of 602 of the first portion 515 in an outward direction away from the central axis 506. A length 606 of each of the thermal barriers 516 may be equal to a distance between an outer surface of the sleeve 510 and an inner surface of the rotor core 502.

A temperature of the target 504 may become elevated during operation of the x-ray tube due to bombardment of the target 504 by an electron beam from a cathode assembly. The heat may be radiated or conducted to other components within a vacuum chamber of the x-ray tube, such as the rotor core 502 and the bearing assembly 508. When additively manufactured, the thermal barriers 516 may be formed from the same material as the rotor core 502 and the bearing assembly 508. In other examples, where the rotor core 502, bearing assembly 508, and thermal barriers 516 are not additively manufactured, the thermal barriers 516 may be formed of an insulating material that inhibits heat transfer from the target 504 to the rotor core 502, or a non-insulating material, such as metal, that at least partially absorbs the heat from the target. By deterring heat transfer to the rotor core 502, heating of the magnets 514 may be hindered, thereby reducing thermal degradation of the magnets 514, e.g., demagnetization, and maintaining a performance of the PMSM. Furthermore, by reducing heating of the magnets 514, less costly magnets with lower heat tolerance may be used, a remanence of the PMSM of may be reduced, and less material may be demanded to form the PMSM while maintaining the PMSM output.

In other examples, as described above with reference to FIG. 3, permanent magnets may be disposed in the sleeve of the bearing assembly to reduce rubbing between the sleeve and shaft of the bearing assembly during deceleration of the rotor. Thermal barriers may also be positioned in the bearing assembly sleeve to reduce heat transfer to the sleeve. A region of the x-ray source 200 of FIG. 2, as indicated by dashed area 250, is shown in detail in FIGS. 8 and 9. A first example configuration 800 and a second example configuration 900 of permanent magnets and thermal barriers are illustrated in FIGS. 8 and 9 respectively.

Turning first to FIG. 8, the sleeve 78 of the bearing assembly may include at least one magnet 802, e.g., a permanent magnet, oriented so that a length 804 of the magnet is parallel with the centerline 70. The magnet 802 may protrude from the outer surface of the sleeve 78, as shown in FIG. 8, or may be recessed into the sleeve 78, in other examples, so that the magnet 802 is flush with the outer surface. The sleeve 78 may include thermal barriers 806 positioned around the magnet 802. The thermal barriers 806 may be arranged between the magnet 802 and the shaft 76 of the bearing assembly as well as between the magnet 802 and the target.

In one example, the thermal barriers 806 may be gaps or slots in the sleeve 78 filled with an insulating material. The thermal barriers 806 may be incorporated into the sleeve 78 when the sleeve 78 and rotor core are additively manufactured, e.g., formed during 3D printing.

Alternatively, thermal barriers may be added as separate parts to the sleeve. For example, as shown in FIG. 9, at least one magnet 902 may be coupled to the outer surface of the sleeve 78 of the bearing assembly via welding, adhesive, etc. The magnet 902 may be oriented so that a length 904 of the magnet 902 is perpendicular to the centerline 70. As such, the magnet 902 may be a protrusion extending perpendicularly away from the outer surface of the sleeve 78. At least one thermal barrier 906 may be arranged between the magnet 902 and the target 48 to inhibit heat transfer via radiation from the target 48 to the magnet 902. The thermal barrier 906 may be formed of an insulating material, similar to the thermal barriers 516 of FIGS. 5 and 6, and may have a height, as defined along the y-axis, at least equal to the length 904 of the magnet 902.

It will be appreciated that the first and second example configurations 800, 900 shown in FIGS. 8 and 9 are non-limiting examples of magnet and thermal barrier configurations in the bearing assembly sleeve. Other examples may include variations in orientation, dimensions, geometries, and quantities of the magnet and thermal barriers.

Figure 10:
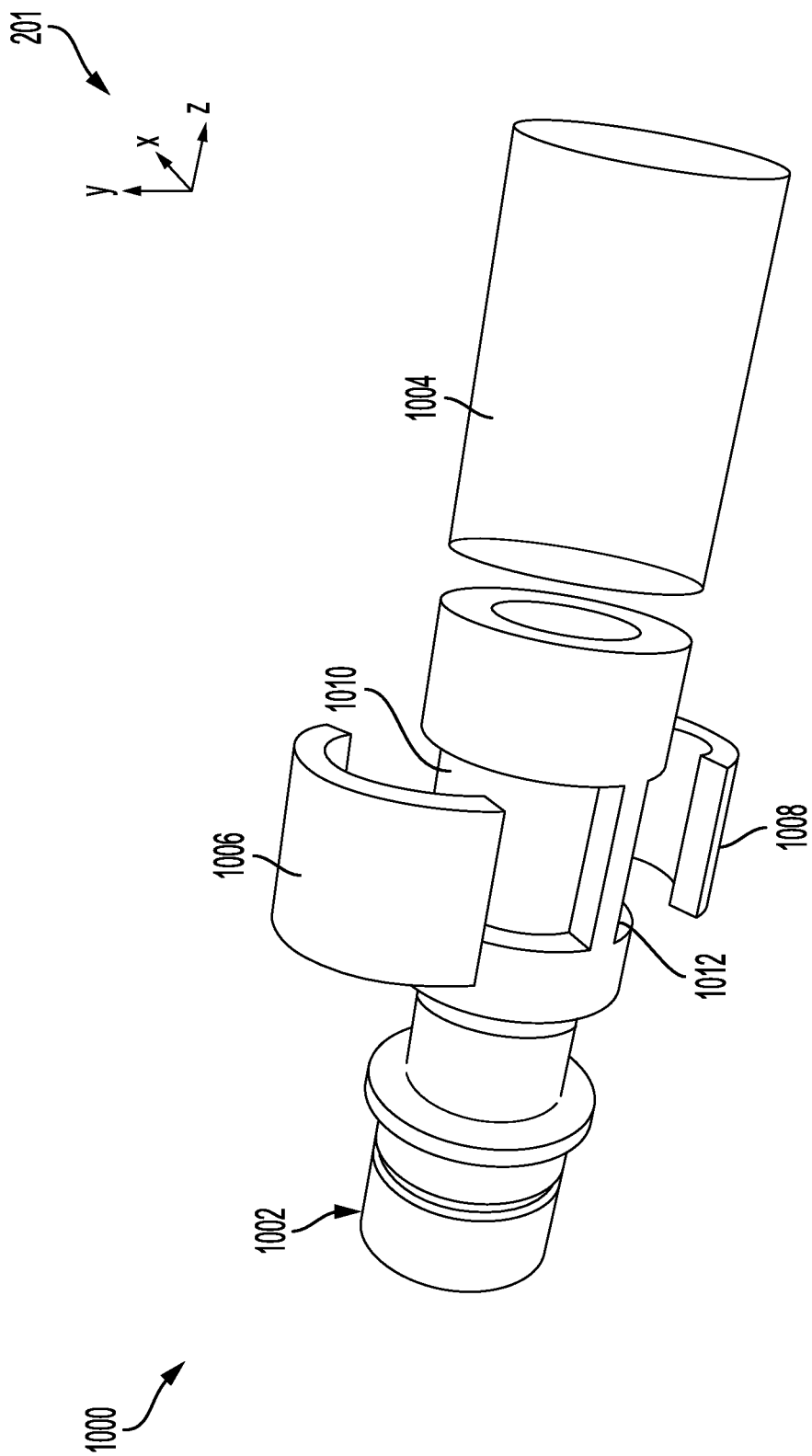
FIG. 10 shows a second example of a rotor core of a permanent magnet synchronous motor (PMSM) for an imaging system.

As described above, variations in a configuration of permanent magnets in a rotor core have been envisioned. In addition, a geometry of the rotor core may also be modified to accommodate, for example, different stator configurations and/or different geometries of a vacuum chamber of an x-ray tube. The rotor core may be fabricated via additive manufacturing to integrate at least one of a retention sleeve and a bearing assembly sleeve with the rotor core in a PMSM. A first example of an alternate configuration of a rotor core 1002 is illustrated in FIG. 10 in an exploded view 1000. A retention sleeve 1004 is also depicted, where the retention sleeve is configured to slide over at least a portion of the rotor core 1002 where a first magnet 1006 and a second magnet 1008 are disposed.

The rotor core 1002, as described above, may be magnetic or non-magnetic and has a first recess 1010 configured to receive the first magnet 1006 and a second recess 1012 configured to receive the second magnet 1008. The first magnet 1006 and the second magnet 1008 may be similarly configured and may each be a semi-circular shell extending around at least a portion of a circumference of the rotor core 1002. The first and second magnets 1006, 1008 may be maintained in the first and second recesses 1010, 1012, respectively, by the retention sleeve 1004.

As described above, when the rotor core 1002 is magnetic, the retention sleeve 1004 may be formed separately of a non-magnetic material and coupled to the rotor core 1002 during assembly. When the rotor core 1002 is non-magnetic, the rotor core 1002 and retention sleeve 1004, as well as a bearing assembly sleeve, may be additively manufactured as a continuous unit. A length of the rotor core 1002 may be reduced compared to a rotor of an induction motor with the same output power and airgap diameter, enabling decreased rotor inertia and faster boost, amongst other benefits described previously.

Figure 11:
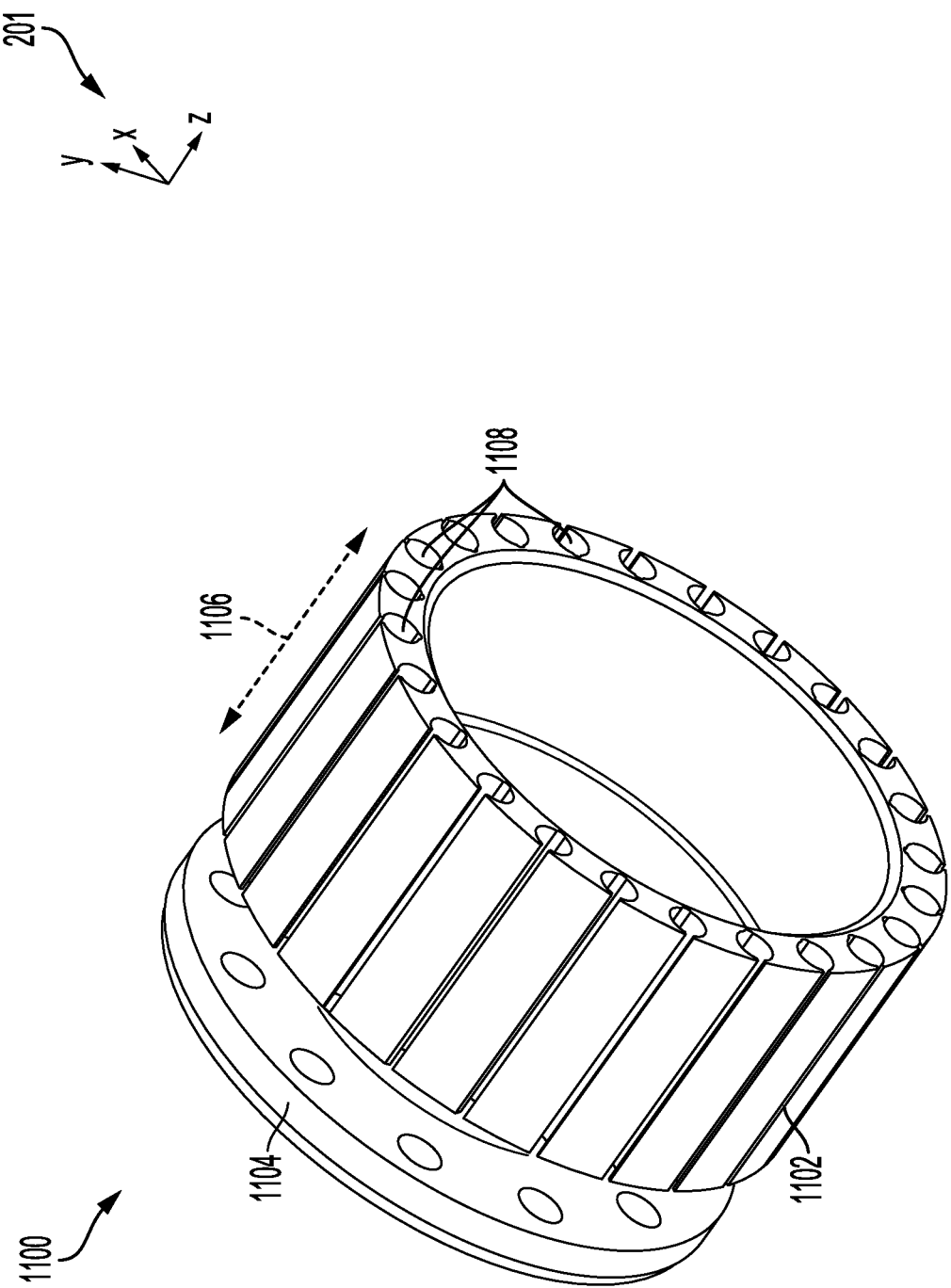
FIG. 11 shows a third example of a rotor core of an induction motor for an imaging system.

A second example of an alternate configuration of a rotor core 1102 is shown in FIG. 11. The rotor core 1102 forms one section of a rotor 1100, such as an induction motor squirrel-cage rotor, and is coupled to a flange 1104, the flange 1104 configured to interface with a bearing assembly of an x-ray tube in which the rotor 1100 is incorporated. As such, the rotor core 1102 may be magnetic (e.g., formed from a magnetic material) and additively manufactured with a bearing assembly sleeve, where the bearing assembly sleeve may also be magnetic (e.g., formed from a magnetic material). In one example, the length 1106 of the rotor core 1102 may be 33.5 mm.

The rotor core 1102 includes through-holes 1108 extending axially along the entire length 1106 of the rotor core 1102. The through-holes 1108 may have circular cross-sections, e.g., along the x-y plane, and a diameter of the through-holes 1108 may be uniform along the length 1106 of the rotor core 1102. The through-holes 1108 may be configured to receive copper or aluminum casting or tubular rods thereof. Though the through-holes 1108 are depicted as circular, in other examples, the through-holes 1108 and magnets may have other geometries besides circular.

As described above, coupling a rotor of a PMSM to a liquid bearing assembly of an x-ray tube may provide various benefits with regards to manufacturing and performance of an imaging system. When the PMSM is implemented in a CT system, such as the CT system 1200 of FIG. 12, the benefits may include precise control and monitoring of a speed and position of the rotor while a gantry of the CT system is rotating, where the x-ray tube with the PMSM is embedded in the gantry.

The control and monitoring of the rotor speed and position may provide effects such as prolonging component life, enhancing image resolution, and increasing x-ray flux in the CT system. In some examples, such effects may be enhanced in other systems capable of providing less than 1 g acceleration for a short time period. However, at least some of the effects, such as target repair and other effects dependent upon target positioning, may be applicable to any type of x-ray imaging system, including stationary systems. For example, a deceleration profile of the rotor may be controlled when rotor speed is accurately known, decreasing a duration at which the rotor is rotating at a low speed conducive to rubbing between the sleeve and the shaft of the liquid bearing assembly of the x-ray tube. Continual rubbing may expedite loss of a contact layer between the sleeve and the shaft. By controlling the deceleration profile of the rotor, the contact layer may be preserved, thereby prolonging a useful life of the liquid bearing assembly.

The controlled deceleration profile may include the rotor reaching zero speed when the x-ray tube is at less than 1 g, such as when the x-ray tube is close to a highest point of a CT gantry rotation. At this point, a g-force due to rotation of the gantry may be −1 g, cancelling Earth's gravitational pull of 1 g. As such, a force causing rubbing of the sleeve against the shaft of the liquid bearing assembly may be minimized.

For example, as shown in FIG. 13, a CT gantry 1300 of a CT system (such as the CT system 1200 of FIG. 12) includes an x-ray source 1302 and an x-ray detector 1304 embedded in the CT gantry 1300. The CT gantry 1300 rotates as indicated by arrows 1306 which causes a radial force, as indicated by arrow 1308, to be exerted on the x-ray source 1302. The radial force is directed outwards, away from a center of the CT gantry 1300 and a magnitude of the radial force may depend on a rotation speed of the CT gantry 1300. The x-ray source 1302 also experiences a gravitational pull, or g-force, as indicated by arrow 1310, which, unlike the radial force, is consistently in a downwards direction.

A resulting force experienced by the x-ray source 1302 is shown in FIG. 14. A diagram 1400 is illustrated in FIG. 14, depicting vectors indicating radial acceleration, gravity, and a force exerted on the x-ray source resulting from a combination of the radial acceleration and gravity vectors. The force may be a cross-product of radial acceleration and gravity. The radial acceleration may vary depending on a position of the x-ray source within the gantry.

Returning to FIG. 13, when the x-ray source 1302 is at a first position where the x-ray source is at or near a top of the CT gantry 1300, the magnitude of the radial force may be similar to the g-force and may oppose the g-force. Thus at this position, the resulting force may be perpendicular to both the radial acceleration and gravity and the x-ray source 1302 may experience a minimal magnitude of the resulting force which may otherwise bias a position of a sleeve relative to a shaft of a bearing assembly of the x-ray source 1302 and cause rubbing. Thus, abrasion between the sleeve and shaft may be reduced at this position.

An example of a method 1500 for decelerating a rotor during operation of a CT imaging system adapted with liquid metal bearings is shown in FIG. 15. For example, the CT imaging system may be the CT system 1200 of FIG. 12, having an x-ray tube and bearing assembly similar to the x-ray source 200 of FIG. 2 and bearing assembly 50 of FIGS. 2 and 3. As shown in FIGS. 5-7 and 10-11, the rotor may include permanent magnets. The CT imaging system may be actively collecting data for image reconstruction or may have recently completed data acquisition, continuing to rotate at high speed. Method 1500 may be conducted in response to a command to deactivate the CT imaging system, e.g., data acquisition is complete and no longer desired. Instructions for carrying out method 1500 may be executed by a control unit, such as the computer 22 of FIG. 1, based on instructions stored on a memory of the control unit.

At 1502, the method includes driving a gantry of the CT system at a speed where radial acceleration is equal to 1 g. For example, the rotor and a target coupled to the rotor may be rotating at a high frequency, such as 90 to 250 Hz and the x-ray source, coupled to the gantry, may be rotating about a subject at 1 Hz. The gantry rotation may be decreased until radial acceleration is 1 g. The rotor deceleration profile is defined at 1504 as a function of time upon radial acceleration reaching 1 g and includes reducing rotor speed at a high speed gradient.

For example, as shown in FIG. 16 in graph 1600, a force exerted on the x-ray tube and rotor by a combination of gravity and radial acceleration, resulting from rotation of the gantry, is depicted at plot 1602 (dashed line) and rotor speed, e.g., a rotational speed of the rotor as the rotor spins within the gantry, is depicted at plot 1604 (solid line). The force, in gravitational units g, is shown along the y-axis relative to time/gantry angle along the x-axis. As the gantry rotates, the force exerted on the rotor varies between 0 g at the top of the gantry and 2 g at the bottom of the gantry.

The deceleration profile may represent a linear deceleration of the rotor that is synchronized to the gantry position. By synchronizing the deceleration profile with the gantry position, the rotor speed reaches zero when the resulting force on the x-ray tube is at a minimum. As indicated at graph 1600, the predefined deceleration profile may be matched with plot 1602 to initiate the deceleration profile at point 1606, allowing linear deceleration of the rotor to a halt to coincide with the x-ray tube being positioned at the top of the gantry, as indicated at point 1608.

The synchronization of the deceleration profile with gantry position minimizes an amount of time that the rotor spends at a low speed that exacerbates rubbing between a shaft and a sleeve of the liquid bearing assembly. For example, when the motor is not implemented as a PMSM, and speed of the motor is not measurable, DC current braking may be used when rotor speed approaches zero to ensure that the rotor comes to a standstill. However, a longer period of time elapses for the rotor to reach zero speed, prolonging the amount of time that the rotor is at a low speed conducive to bearing assembly rubbing. As another example, the rotor, when speed is not measurable, may be allowed to coast to a standstill, further promoting rubbing between the bearing assembly sleeve and shaft.

Based on the deceleration profile defined at 1504 in FIG. 15, starting positions of the gantry and the rotor, where detection of the gantry and rotor at their respective starting positions initiates the deceleration profile, are inferred at 1506 and used as a reference to compare with a current position of the moving gantry and rotor. For example, the starting position may be a position estimated to result in the x-ray tube being located close to a top of the gantry when the rotor reaches zero speed. The starting positions may be updated by implementing a continuously updating feedback loop that measures when the rotor actually reaches zero speed and compares the actual positions of the gantry and rotor with the estimated positions. The measurement data may be used to adjust and correct the estimated starting positions of the rotor and gantry to reflect the actual positions.

The predetermined deceleration profile is initiated at 1508 when the gantry and rotor are detected to reach the starting position. Deceleration of the rotor begins according to the deceleration profile. The rotor reaches zero speed when the x-ray tube is close to the top of the gantry. As described above, at the top position of the gantry, a gravitational force on the rotor may be offset by a radial acceleration force, resulting in a net acceleration of 0 g.

Upon the rotor reaching zero speed, the rotor drive is halted at 1510. In some instances, the rotor may not reach zero speed at the top of the gantry. Instead, a stopping position of the rotor may deviate from the top by a small amount, such as 1-10% of a circumference of the gantry. The rotor speed as the rotor passes through the top may be measured and the measurement used in the feedback loop to update and correct the deceleration profile and/or the starting point of the deceleration profile.

Correcting the deceleration profile may include incorporating a squeeze film effect. The squeeze film effect occurs when a thin layer, or film, of fluid is trapped between relatively large, parallel surfaces when the surfaces are moving relative to one another. A period of time may elapse before the film is "squeezed" out from between the surfaces enough that the surfaces touch. When the squeeze film effect is included in the synchronization of the deceleration profile and gantry position, the deceleration timing may be adjusted so that the rotor does not reach zero speed at an estimated optimal position. For example, the rotor may reach zero slightly after the optimal, 0 g position. When the squeeze film effect is incorporated, fast rotor deceleration may be demanded due to a reduction in hydrodynamic lift as rotor speed is decreased. The squeeze film effect may be adapted into the synchronization during a final portion of rotor deceleration when rotor speed is near zero. In one example, stopping the rotors in less than 2.5 s from 10 Hz may reduce rubbing between the shaft and sleeve of the bearing assembly.

Figure 17:
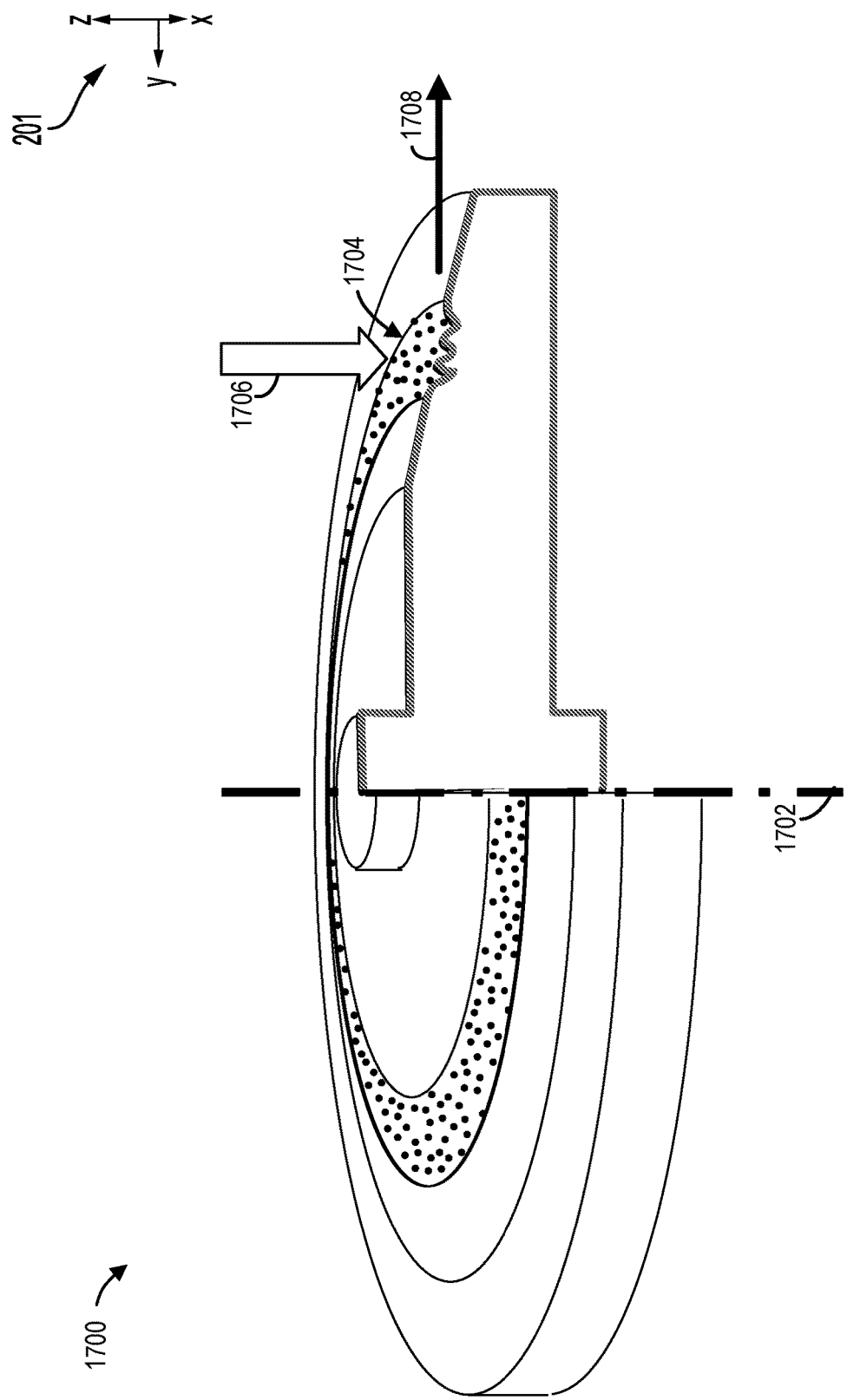
FIG. 17 shows a first example of a target for an x-ray tube, from a partial cut-away view, with an imperfection region.

In addition to precise control of rotor speed, accurate monitoring of rotor position may be leveraged to account for target imperfections, troubleshoot high voltage (HV) instability, enable target repair, and provide spot wobble, fast kV, and z-wobble, thereby enhancing image quality. For example, FIG. 17 shows a partial cutaway view of an example of a target 1700, e.g., an anode, of an x-ray tube implemented in an imaging system. In one example, the target 1700 may be the target 48 of FIG. 2. The target 1700 may be disc-shaped with a central axis of rotation 1702.

In some examples, the target 1700 may have at least one imperfection region due to manufacturing inconsistencies or due to operation of the x-ray tube, such as excessive and/or repeated bombardment of the target 1700 by electron beams. As shown in FIG. 17, the target 1700 may include an imperfection region 1704 that forms a ring along a surface of the target 1700. In some examples, the imperfection region 1704 may create an uneven and textured area along the target surface and may coincide with a focal track, e.g., an area where an electron beam, as indicated by arrow 1706, strikes the surface of the target 1700. When the electron beam impinges the target 1700 at the imperfection region 1704, as indicated by arrow 1706, a resulting x-ray beam, indicated by arrow 1708, emitted from the imperfection region 1704 may alter an overall x-ray beam spectrum generated by the target 1700. The change in the x-ray beam spectrum may result from, for example, increased self-filtration of the target 1700.

By knowing a position of a rotor of the x-ray tube, an exact position of the target 1700 may also be known. The target position may be synchronized with a view acquisition start time or exposure acquisition start time and used to calibrate operating parameters for a specific imaging subject. Spectral and positional deviations of the emitted x-ray beam, resulting from target deviations, target imperfections, etc., may be corrected for in the calibrated operating parameters.

Figure 18:
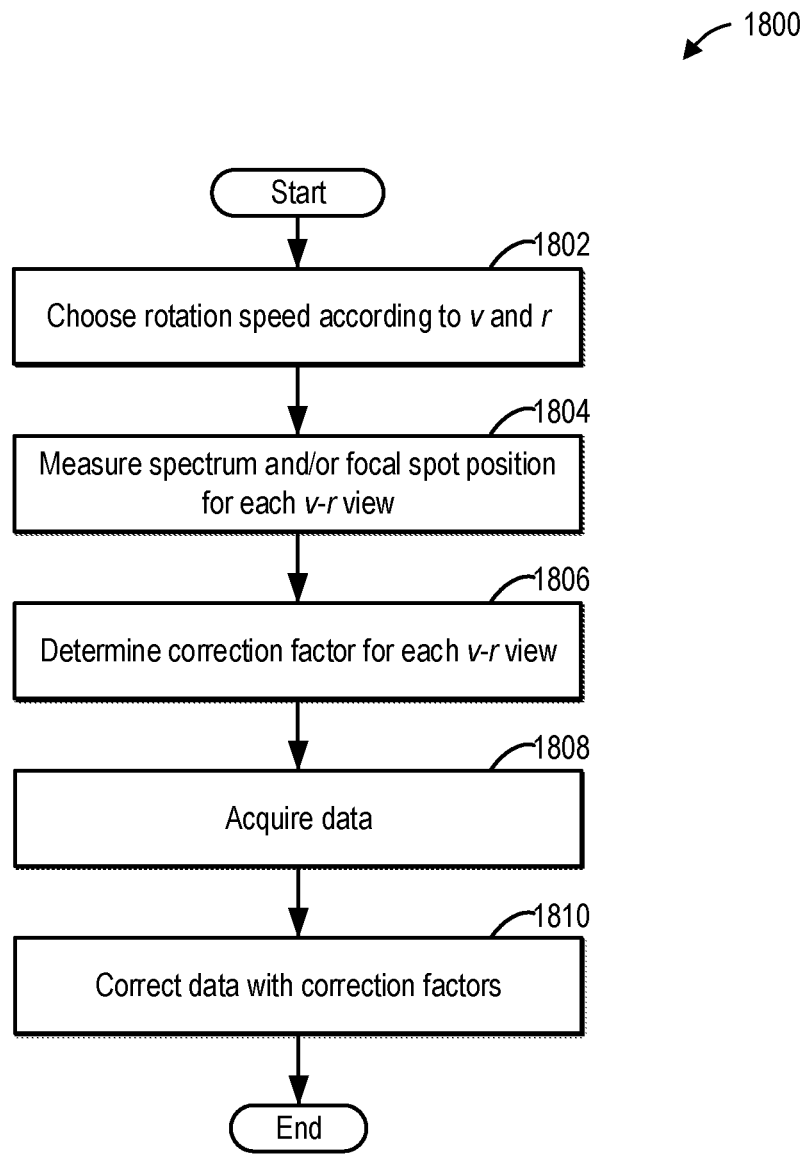
FIG. 18 shows an example of a method for correcting for an imperfection region in a target for an x-ray tube.

An example of a method 1800 for accounting for spectral and positional deviations of the target, e.g., imperfection regions in the target such as the imperfection region 1704 of FIG. 17, during operation of the imaging system is shown in FIG. 18. Method 1800 may be implemented, for example, prior to scanning an object, e.g., a patient, to calibrate the imaging system. The imaging system may be adjusted to a calibration mode. In one example, the imaging system may be the CT system 1200 of FIG. 12, having a target and bearing assembly similar to the target 1700 of FIG. 17 and bearing assembly 50 of FIGS. 2 and 3. The target may include at least one imperfection region, as illustrated in FIG. 17. The bearing assembly and/or a rotor, driving rotation of the target, may include permanent magnets. Instructions for carrying out method 1800 may be executed by a control unit, such as the computer 22 of FIG. 1, based on instructions stored on a memory of the control unit.

Figure 19:
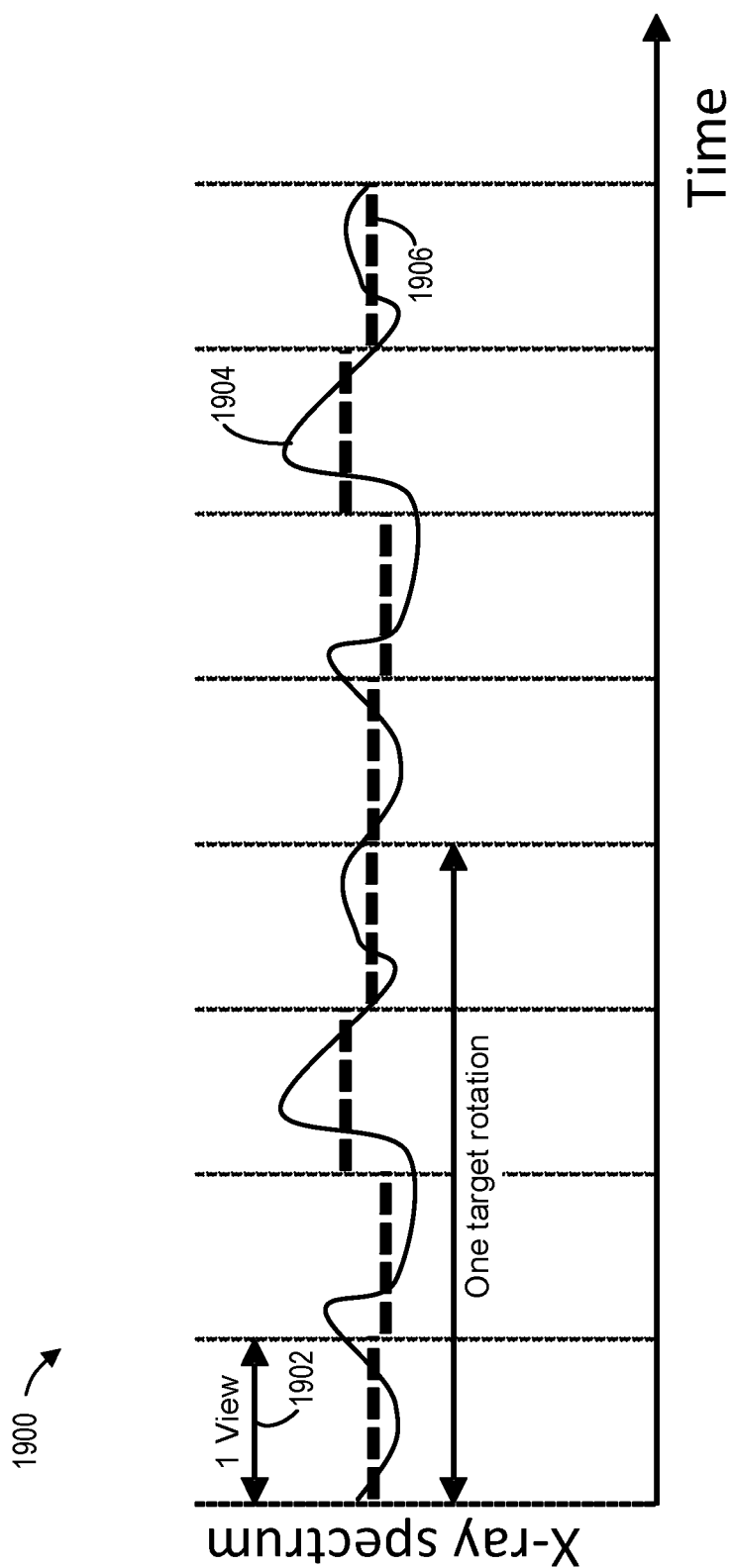
FIG. 19 shows a second graph plotting x-ray spectrum generation by a target with imperfection regions over time.

At 1802, the method includes choosing a rotation speed of the target. The rotation speed may be selected so that an integer number of views v may fit within an integer number of target rotations r. Each view may be a group of x-ray attenuation measurements obtained by a detector array at a given angle. For example, as shown in FIG. 19 in graph 1900, an x-ray spectrum generated by the target is plotted relative to time. Time may be divided into increments 1902, each increment representing time for one view v. A time for one rotation of the target may be a period of time in which an integer number of views may be obtained. For example, in graph 1900, the target rotation may include four views.

An actual, e.g., acquired from data, x-ray spectrum (as characterized by one or more parameters, such as by effective kVp) is shown schematically in graph 1900 at plot 1904. Plot 1904 illustrates a meandering and non-uniform x-ray spectrum, further depicted by an approximated spectrum at plot 1906. The variations in the x-ray spectrum may correspond to variations in a focal spot position of the x-ray beam, where the variations lead to poor image quality if left uncorrected.

Returning to FIG. 18, the x-ray beam spectrum and/or focal spot position of the x-ray beam emitted by the target is measured at 1804 for each of the predetermined v-r views. The x-ray beam may be altered due to interaction with the at least one imperfection region. Correction factors are determined at 1806 for each of the v-r views to account for spectral deviations arising from the at least one imperfection region and includes incorporating the synchronized target position with the view acquisition start time. The correction factors may be determined based on the measured values of the spectrum and/or focal spot position.

At 1808, the method includes acquiring data from a subject, such as a patient or an object. Acquiring data may include using the imaging system to irradiate the subject with the x-ray beam to obtain an x-ray image of the subject. The acquired data is corrected based on the predetermined correction factor for each v-r view at 1810. In this way, imperfection regions in the target that may otherwise lead to deviation in the focal spot position or variation in the x-ray beam spectrum may be accounted and corrected for in the acquired data. Continual calibration of the x-ray tube may provide more accurate results and therefore enhanced image quality.

Controlling and/or accurate monitoring of a position of a rotor, and therefore of a target, of an x-ray tube may also assist in troubleshooting high voltage (HV) instability issues. HV instability events may include short circuits occurring through a vacuum inside the x-ray tube as well as through oil or other materials, e.g., at connector interfaces. Detection of multiple HV events at a same target position may be indicative of a problem at the target rather than at other x-ray tube components, such as at a connector. As an example, the target may have a localized imperfection, as shown in FIG. 20.

Figure 20:
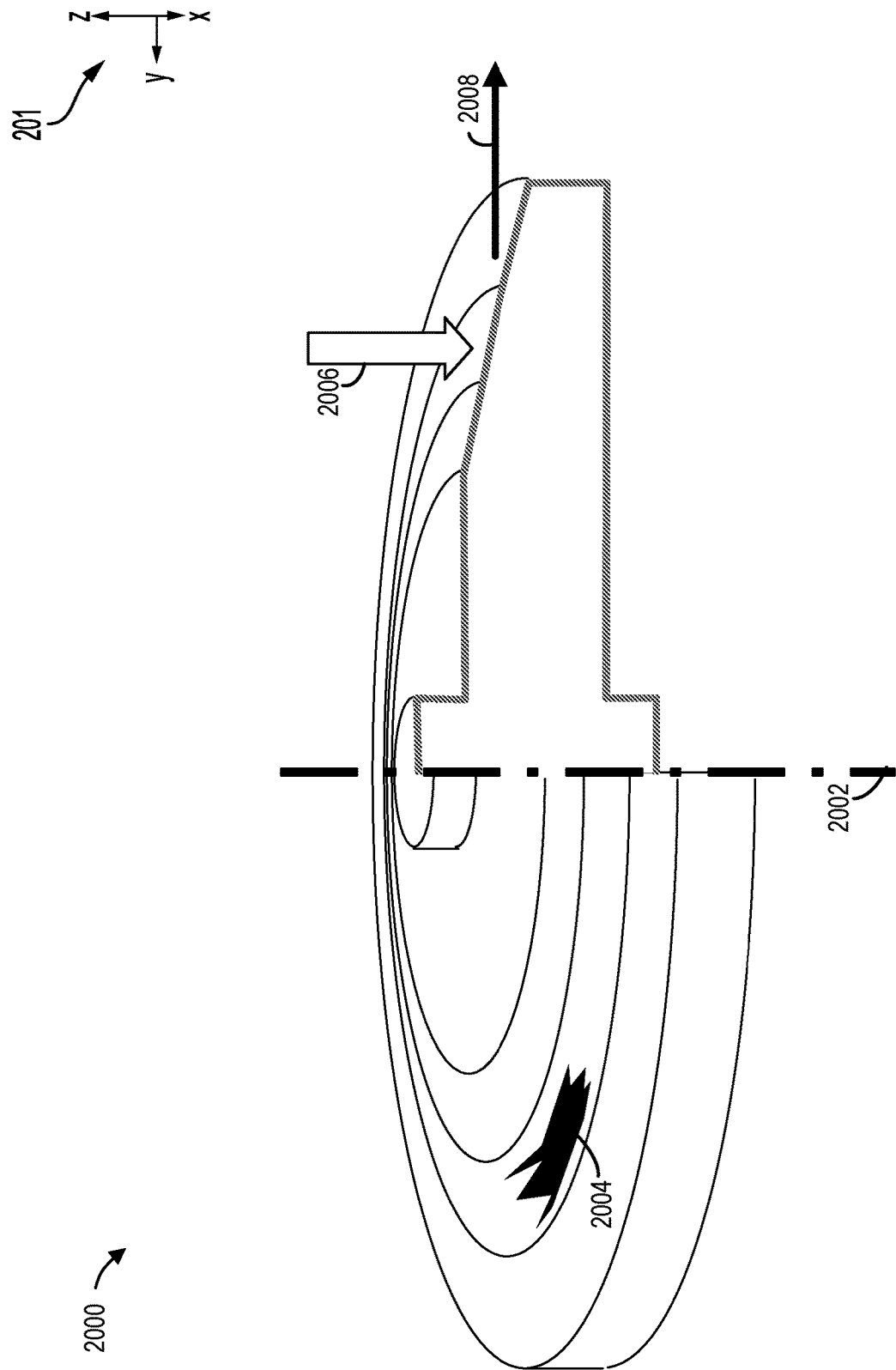
FIG. 20 shows a second example of a target for an x-ray tube, from a partial cut-away view, with a localized imperfection.

In FIG. 20, a target 2000 may be similar in geometry to the target 1700 of FIG. 17, having a central axis 2002. The target 2000 may have a localized imperfection 2004 rather than or in addition to an imperfection region as shown in FIG. 17. An electron beam, as indicated by arrow 2006, may strike the localized imperfection 2004 at a particular frequency as the target 2000 rotates about the central axis 2002. An emitted x-ray beam, as indicated by arrow 2008, may be altered due to periodic interaction with the localized imperfection 2004. Furthermore, in some instances, interaction of the electron beam with the localized imperfection 2004 may result in an HV instability event.

When an HV instability event is detected, an HV generator may transiently shut off HV power supply to the x-ray tube. A short circuit (or "arc") resulting from the HV instability event may be allowed to dissipate over a period of time such as 0.1 ms to 10 ms. After the period of time elapses, the HV generator may increase the voltage to a desired tube voltage, e.g., a same tube voltage as prior to the HV instability event. As multiple HV instability events may follow one another closely, a total duration of a process for turning off HV power and reinstating tube voltage may occur over a time range of 0.2 ms to 100 ms. During the process time for turning off HV power, useful images may not be acquired due to lack of emitted x-ray beams, thus leading to an increased likelihood of image artifacts.

Figure 21:
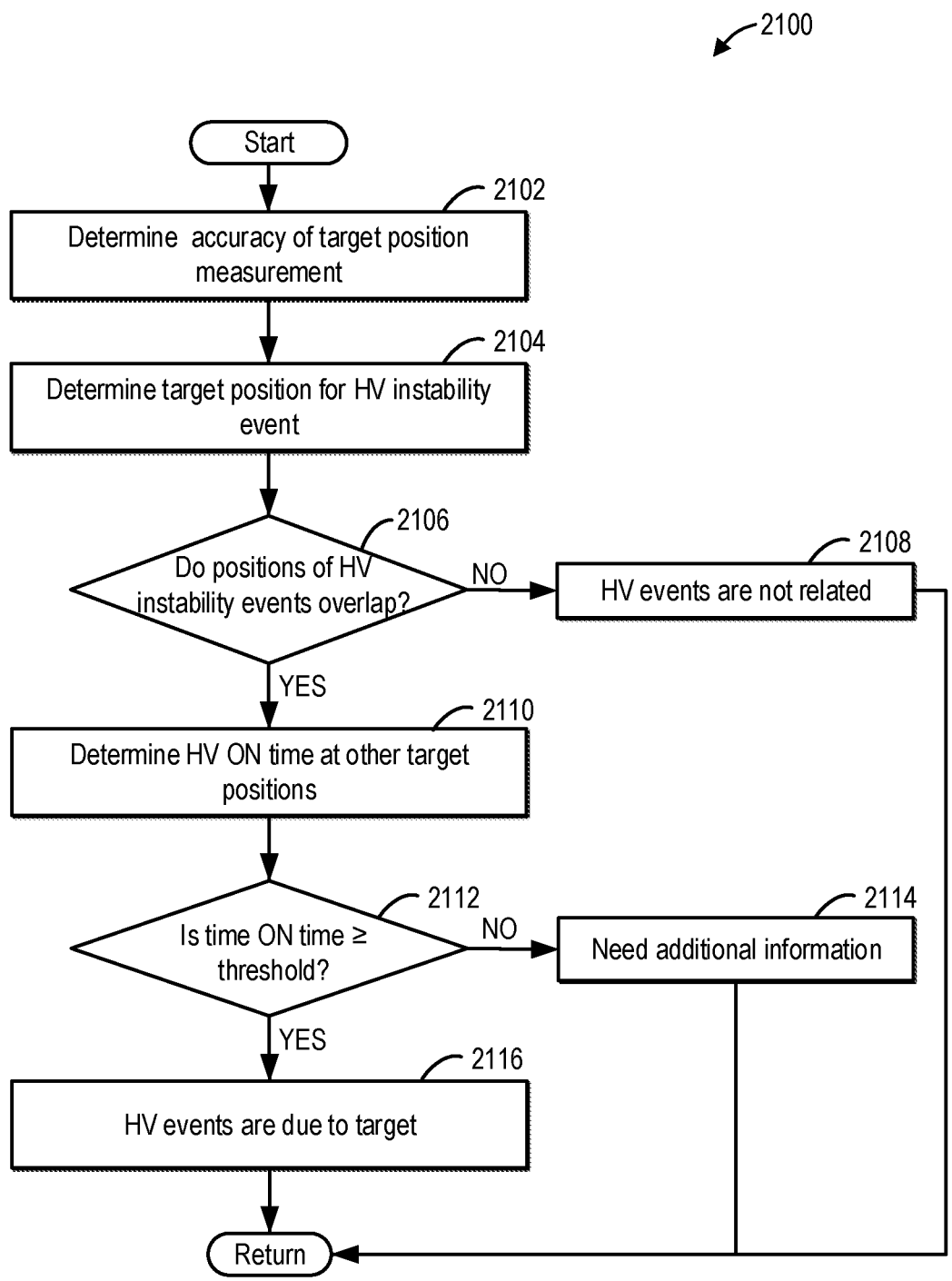
FIG. 21 shows an example of a method for evaluating high voltage (HV) instability events.
Figure 22:
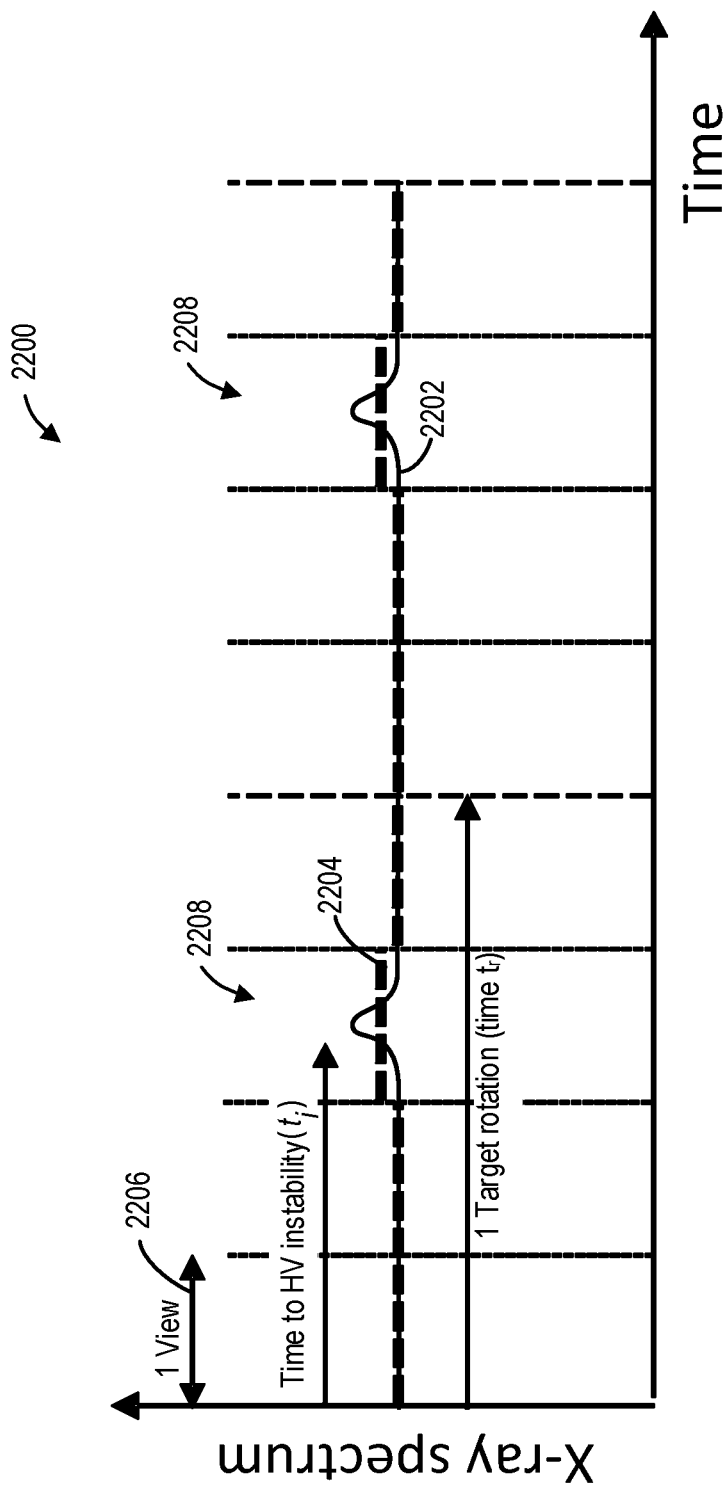
FIG. 22 shows a third graph plotting x-ray spectrum generation by a target exhibiting HV instability over time.

By determining that HV instability events and variations in the x-ray spectrum result from a localized imperfection in the target, issues with obtaining high quality data may be quickly rectified by, for example, replacing or treating the target, or replacing the x-ray tube. A method 2100 for identifying a source of HV instability events during operation of an imaging system is shown in FIG. 21. In one example, the imaging system may be the CT system 1200 of FIG. 12, having an x-ray tube with a target and bearing assembly similar to the target 2000 of FIG. 20 and bearing assembly 50 of FIGS. 2 and 3. The target may include at least one localized imperfection, as illustrated in FIG. 20. The rotor, driving rotation of the target, may include permanent magnets. Instructions for carrying out method 2100 may be executed by a control unit, such as the computer 22 of FIG. 1, based on instructions stored on a memory of the control unit.

At 2102, the method includes determining an accuracy of a target position measurement of the x-ray tube. The accuracy may be determined by rotating a target with a known single defect at a known position, and configured to cause HV instability, and measuring a rotation angle at which the HV instability occurs during successive rotations of the target. The accuracy and precision of the target position may then be inferred by comparing the measured positions at which the HV instability occurs relative to the known position of the defect.

Using the target position measurement, a target position of detected HV instability events is estimated at 2104. For example, as shown in graph 2200 in FIG. 22, a parameter such as an x-ray spectrum or another HV instability parameter is plotted with respect to time in an actual plot 2202 of the spectrum and an approximated plot 2204 of the spectrum. Similar to graph 1900 of FIG. 19, time may be divided into increments 2206, each increment representing time for one view v. A time for one rotation of the target, e.g., $t_r$, may be a period of time in which an integer number of views may be obtained. For example, in graph 2200, the target rotation may include four views.

HV instability events 2208 may occur when amplitudes exceed a threshold, depicted as occurring proximate to peaks in the actual plot 2202 of the spectrum and occur at time $t_i$ at a third increment of the increments 2206 included in each rotation, $t_r$, of the target. A target position at each of the HV instability events 2208 may be estimated based on the ratio $t_i/t_r$ of the instability time $t_i$ and the rotation time $t_r$. As the HV instability events 2208 occur at the same target position, the HV instability events are related and attributable to a common source in graph 2200. In other examples, however, the HV instability events 2208 may be detected at different time increments of each target rotation, $t_r$. For example, during a first rotation, a first HV instability event may occur at a second increment of $t_r$ and during a second rotation, a second HV instability event may occur at a fourth time increment of $t_r$. In such an instance, $t_i/t_r$ is not the same for each of the first and second HV instability events and the events may be therefore deemed unrelated.

Returning to FIG. 21, at 2106, the method includes evaluating whether the estimated target positions, based on detection of the last n HV instability events, overlap (where n is a number of HF instability events). A chosen value of n may be a tradeoff between increased detection accuracy, when the value of n is large, with a decreased amount of time for a decision to be made when the value of n is small. For example, the target position measurements of the HV instability events may overlap if the estimated position measurements are within a threshold, such as 5% to 10% of a full target rotation. If the positions do not overlap, the method proceeds to 2108 to confirm that the HV instability events are not related to one another and other actions to identify the sources of the HV instability events may be demanded. The method ends.

If the positions are determined to overlap, the method continues to 2110 to measure a period of time that the HV instability events persists at other target positions. The other target positions may be position measurements that do not overlap with two or more overlapping HV instability events. The period of time that the HV instability events at other target positions are each compared to a threshold period of time at 2112. The threshold period of time may be a multiple of a measured duration of time elapsed during the overlapping HV instability events, or a fixed number of target rotations during which no HV instability events at other target positions are detected. If the durations of the HV instability events at other target positions are not at least equal to or greater than the duration of the overlapping HV instability events, the method proceeds to 2114 and is unable to conclude whether or not the HV instability events are due to the target. The method returns to the start and may be run again with a larger value of n.

If the duration of the non-overlapping HV instability events are at least equal to the duration of the overlapping HV instability events, the method continues to 2116 to provide confirmation that the non-overlapping HV instability events may result from imperfections or issues with the target. The confirmation may be sent, via a communication link, to a central data location to be saved in a log file along with corresponding information about the x-ray tube. The method ends.

As described above, method 2100 provides a routine for troubleshooting HV instability issues. Although target imperfections, e.g., the localized imperfection 2004 of FIG. 20, may increase a likelihood of HV instability, a single passage of the electron beam over the target imperfection may not create an HV instability each time. Thus, a value of n may be selected based on an expected (or tolerable) rate of HV instability events. Increasing the value of n may provide more accurate results but may increase a measurement and evaluation time.

Figure 23:
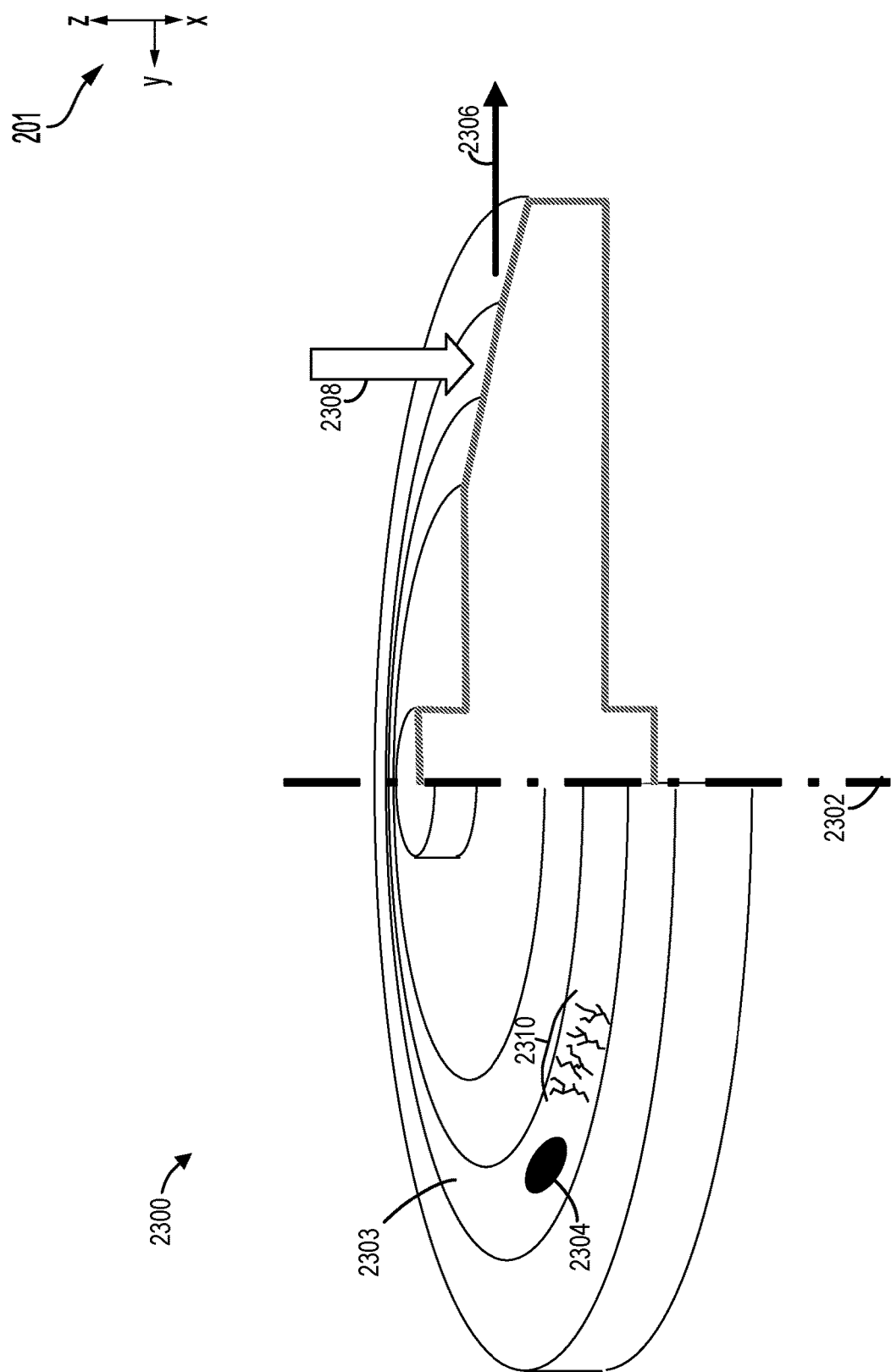
FIG. 23 shows a third example of a target for an x-ray tube, from a partial cut-away view, with an impurity and cracks.

In other examples, accurate knowledge of a target position during operation of an x-ray tube in an imaging system may enable impurity removal and/or target repair. As an example, a target 2300 is depicted in FIG. 23 with a central axis 2302 and a localized impurity 2304 positioned along a focal track 2303 of the target 2300. The impurity 2304 may be formed of a material that is different from a material of the target and causes variations in an x-ray beam, indicated by arrow 2306, emitted when an electron beam, indicated by arrow 2308, strikes the target 2300. Additionally or alternatively, the impurity 2304 may generate a HV instability event.

Figure 24:
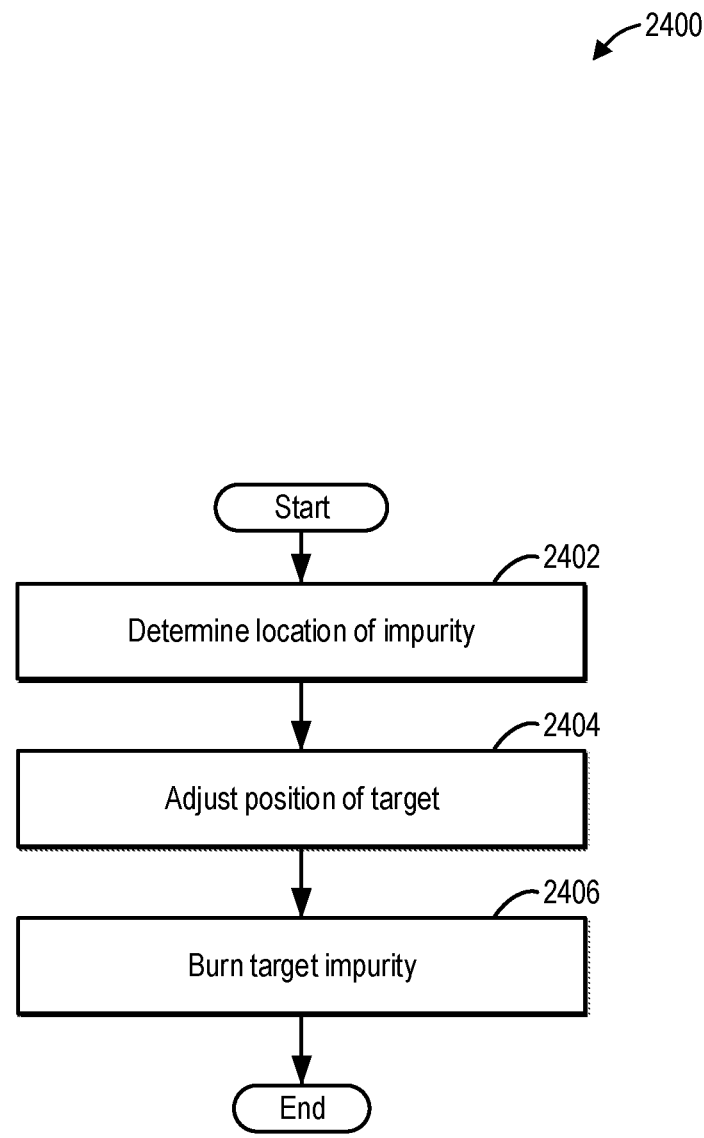
FIG. 24 shows an example of a method for removing an impurity from a target.

By knowing a position of the target when the HV instability event occurs, the impurity 2304 may be removed by positioning the target to a predetermined position and using a low tube current to burn the impurity 2304. An example of a method 2400 for impurity removal from a target of an x-ray tube is shown in FIG. 24. In one example, the x-ray tube may be included in an imaging system such as the CT system 1200 of FIG. 12, having an x-ray tube with a target and bearing assembly similar to the target 2300 of FIG. 23 and bearing assembly 50 of FIGS. 2 and 3. The target may include at least one localized impurity, as illustrated in FIG. 23. The bearing assembly and/or a rotor, driving rotation of the target, may include permanent magnets. Instructions for carrying out method 2400 may be executed by a control unit, such as the computer 22 of FIG. 1, based on instructions stored on a memory of the control unit.

At 2402, the method includes determining a location of the impurity. For example, the location of the impurity may correspond to a target position as determined via method 2100 of FIG. 21, based on occurrence of an HV instability event. The method continues to 2404 to adjust the position of the target, for example to a specific target angle, to focus an electron beam on the impurity. The impurity is burned at 2406 by applying the electron beam at a low current, thereby removing the impurity and preparing the target the subsequent use. The method ends.

Controlling and/or monitoring of the target position may also be leveraged for target repair. For example, returning to FIG. 23, the target 2300 may additionally or alternatively have cracks 2310 positioned along the focal track 2303 which may form as a result of repeated and/or uneven heating of the target 2300. The cracks 2310 may interact with the electron beam, as indicated by arrow 2308, and cause strong spectral deviations. If the cracks 2310 are not repaired within a timely manner, the cracks 2310 may grow and lead to a target burst, e.g., disintegration of the target 2300. The cracks 2310 may be repaired via a method 2500 as shown in FIG. 25, which may be similar to method 2400 of FIG. 24.

Figure 25:
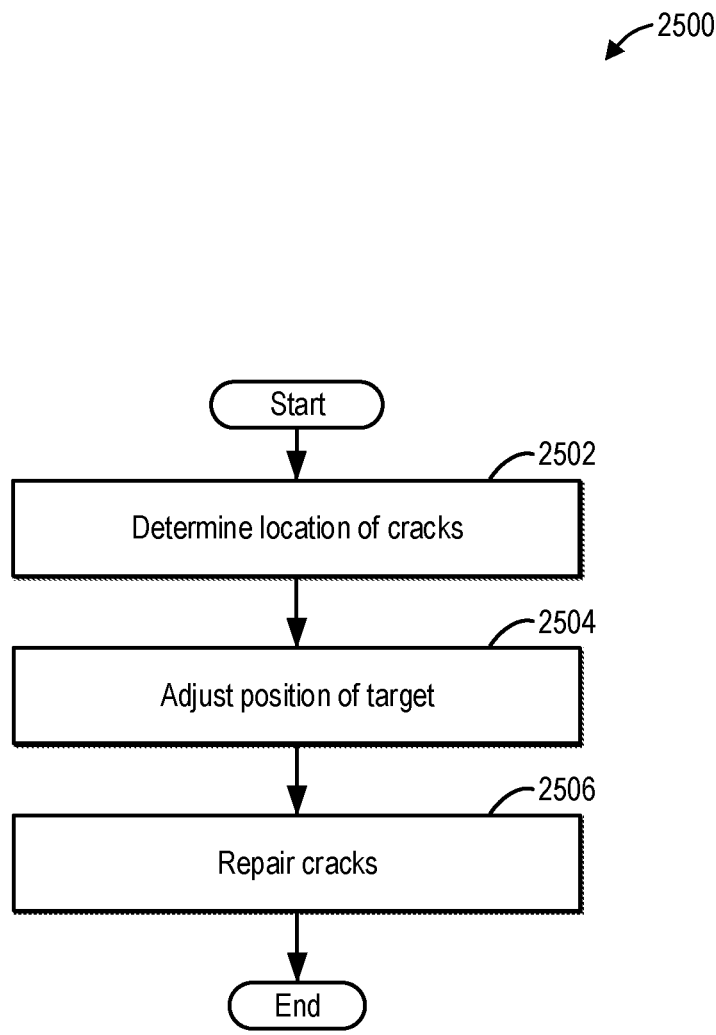
FIG. 25 shows an example of a method for repairing cracks in a target.

Method 2500 of FIG. 25 may be used to repair cracks in a target of an x-ray tube. In one example, the x-ray tube may be included in an imaging system such as the CT system 1200 of FIG. 12, having an x-ray tube with a target and bearing assembly similar to the target 2300 of FIG. 23 and bearing assembly 50 of FIGS. 2 and 3. The target may include at least one set of cracks, as illustrated in FIG. 23. The bearing assembly and/or a rotor, driving rotation of the target, may include permanent magnets. Instructions for carrying out method 2500 may be executed by a control unit, such as the computer 22 of FIG. 1, based on instructions stored on a memory of the control unit.

At 2502, the method includes determining a location of the cracks. For example, the location of the cracks may correspond to a target position as determined via method 2100 of FIG. 21, based on detection of spectral deviations. The method continues to 2504 to adjust the position of the target, for example to a specific target angle, to focus an electron beam on the cracks. The cracks are repaired by treatment with an electron beam at 2506, as one example. The method ends.

Various approaches may be implemented for repairing the target. For example, a large area with cracks may be treated by slow continuous heating using the electron beam. Alternatively, cracks occurring over small areas may be repaired by pulsed heating. The treatment process may depend on a capability of the x-ray tube with regards to electron beam steering, beam size control, beam energy control, and ability to provide short pulses.

Another benefit of accurate control and/or monitoring of an x-ray tube target position, as well as target speed, includes enabling focal spot wobble along a z-axis without electron beam deflection. Conventional techniques for focal spot wobble may include varying a focal spot of an electron beam, tracing a focal track along a surface of the target, between two positions on the target in a direction tangent to the focal track. The electron beam focal spot may be varied by deflecting the beam using deflection coils and/or plates. The varying of the focal spot, e.g., focal spot wobble may enhance image quality and resolution for CT images. However, wobbling the focal spot may generate large quantities of heat at the target, degrading x-ray tube performance and peak power capability.

Figure 26:
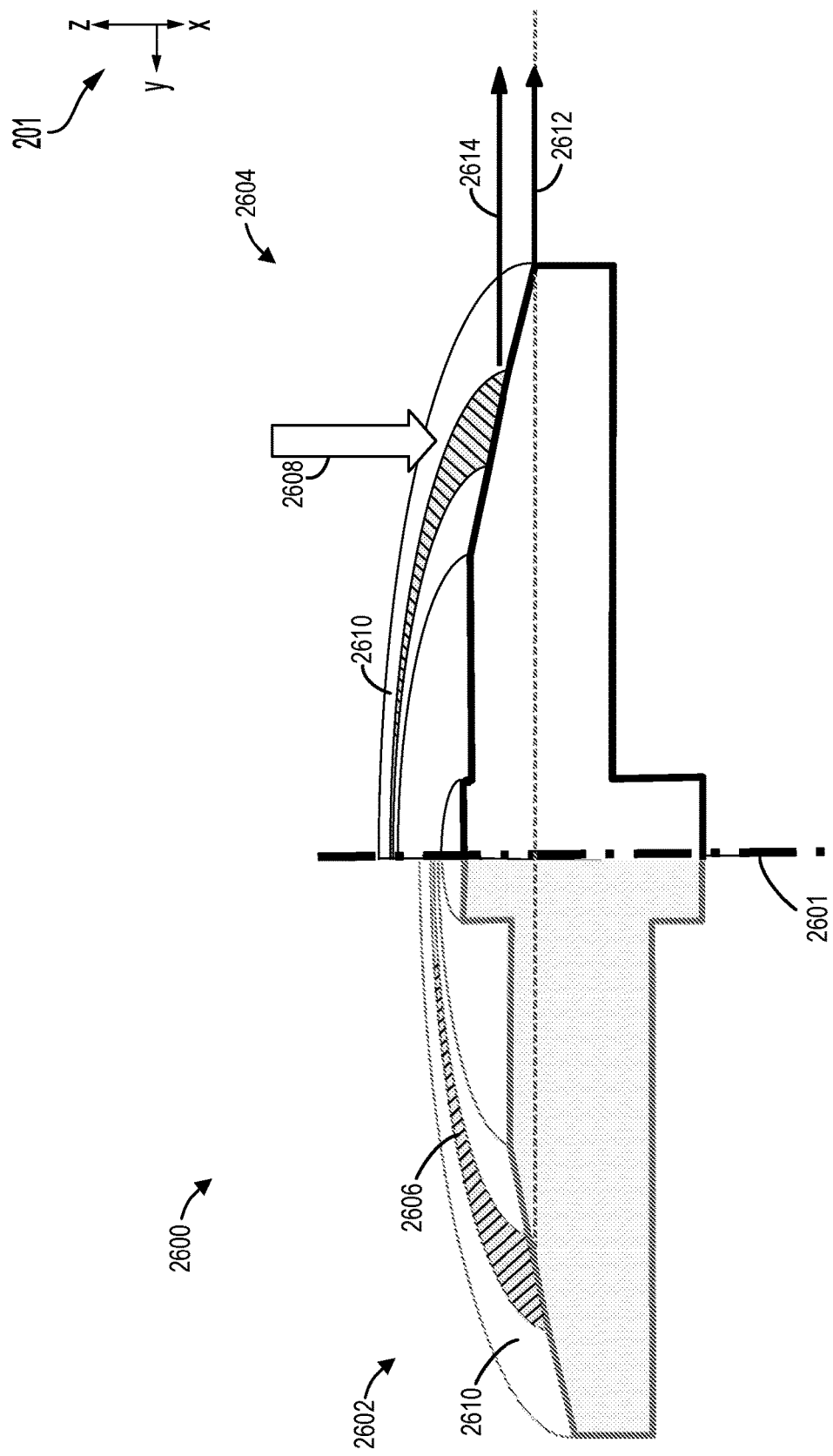
FIG. 26 shows a fourth example of a target for an x-ray tube, from a cut-away view, configured to provide focal spot wobble.

As an alternative, a target 2600 with more than one segment may be used, as shown in FIG. 26. The target 2600 has a first segment 2602 and a second segment 2604, the first and second segments 2602, 2604 on opposite sides of a central axis 2601 of the target 2600. However, other examples of the target may include more than two segments such as 3 or 4 segments. The central axis 2601 may, in one example, be a z-axis 2601 of an imaging system. A circular focal track 2606, along which an electron beam, as indicated by arrow 2608, may be focused, is depicted along an upper surface 2610 of the target 2600, extending continuously across both the first and second segments 2602, 2604 and centered about the z-axis 2601.

The first segment 2602 and the second segment 2604 are positioned offset to one another along the z-axis 2601. For example, the upper surface 2610 of the second segment 2604 is higher along the z-axis than the upper surface 2610 of the first segment 2602. As the target 2600 rotates, the electron beam may be wobbled by interacting with the focal track 2606 along the first segment 2602 and the second segment 2604 in an alternating manner. When the electron beam strikes the first segment 2602 of the target 2600, a first x-ray beam 2612 may be emitted with a first angle relative to the target. The electron beam strikes the second segment 2604 of the target 2600 when the target 2600 rotates 180 degrees, emitting a second x-ray beam 2614 with a second angle relative to the target that is different from the first angle due to the different positioning of the second segment 2604 relative to the first segment 2602 along the z-axis. By acquiring imaging data from two x-ray beams emitted from different focal track positions along the z-axis, focal spot wobble is enabled without demanding electron beam deflection.

Monitoring the target position and speed during focal spot wobble using the target 2600 may allow accurate assignment of an acquired view to a corresponding segment and angle of the target 2600. Thus, the acquired views, alternating between the first and second segments 2602, 2604, may be processed to increase resolution and remove aliasing artifacts in resulting x-ray images without demanding electron beam deflection.

Figure 27:
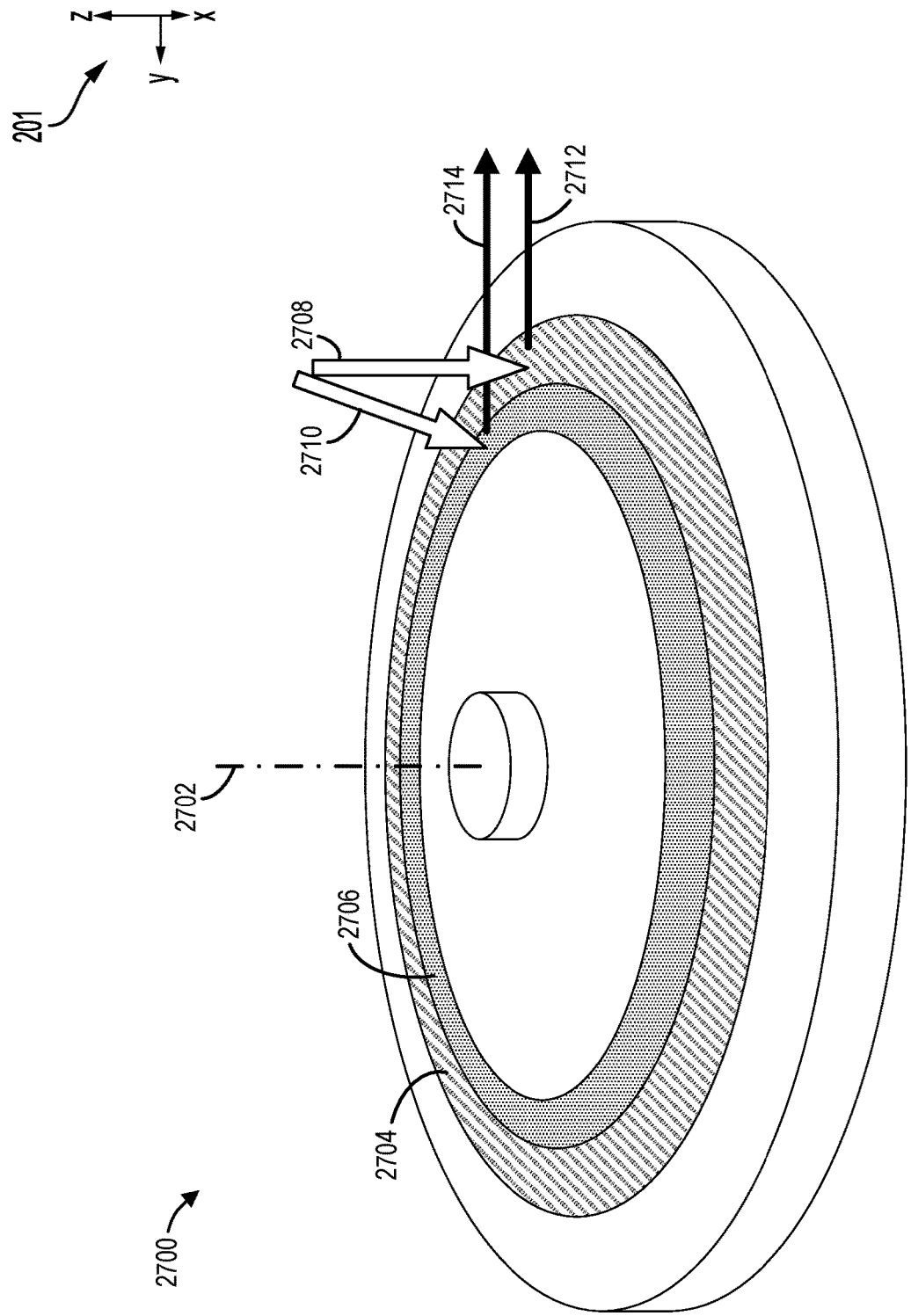
FIG. 27 shows a fifth example of a target for an x-ray tube configured to provide z-wobble.

Accurate monitoring of an x-ray tube target position may also be used for z-wobble with electron beam deflection. As shown in FIG. 27, a target 2700 may have a central axis 2702 that is also aligned with the z-axis 2702. Rather than distinct segments, the target 2700 may have a uniform upper surface with a first focal track 2704 and a second focal track 2706, the focal tracks concentric with one another, with the first focal track 2704 circumferentially surrounding the second focal track 2706. In other examples, the target 2700 may have more than two focal tracks.

A duration of time for a rotation of the target 2700 may be synchronized to an odd multiple of half of a z-wobble period, where the z-wobble period includes two views of equal duration, the first view set on one of the tracks and the second view set on the other track. An electron beam, indicated at a first angle by arrow 2708 and at a second angle by arrow 2710, may alternate between striking and heating the first focal track 2704 and the second focal track 2706. As such, a spot along either of the focal tracks is not heated twice on two consecutive rotations. The spot may cool over a period of time elapsed for the target 2700 to rotate twice before interacting with the electron beam again.

The interaction of the electron beam at the first angle, indicated by arrow 2708, with the first focal track 2704 results in emission of a first x-ray beam 2712 at a first time $t_1$. The interaction of the electron beam at the second angle, indicated by arrow 2710, with the second focal track 2706 results in emission of a second x-ray beam 2714 at a second time $t_2$ where $t_1 \neq t_2$. The first and second x-ray beams 2712, 2714 may be used as described above to increase image resolution and remove aliasing artifacts in resulting x-ray images. By alternating the electron beam angle to interact with the first and second focal tracks 2704, 2706, heat generated by electron beam deflection may be distributed evenly, giving each heated point two full target rotations for cooling before being heated again, thus reducing target degradation. In contrast, when target rotation is not synchronized to the spot wobble period, the heated point may only cool over a single target rotation. In some examples, the electron beam may be turned off during transitions between the focal tracks, to allow an area between the two focal tracks to also cool over two target rotations before reheating. Additionally, the heat distribution provided by adapting the target with more than one focal track may allow higher beam power to be applied, thereby increasing both x-ray flux and image resolution.

Knowledge of a position of an x-ray tube target may additionally benefit fast kV switching applications. In fast kV switching, CT images may be obtained by switching power between two different energy levels, corresponding to low and high tube voltages, which may occur multiple times during a rotation of the target. The switching between low and high tube voltage may provide spectrally resolved x-ray images with high temporal and spatial resolution. However, a spectral separation may be lower than desired due to spectral emissions arising from insufficient difference between low and high tube voltage or due to long voltage transition durations.

Figure 28:
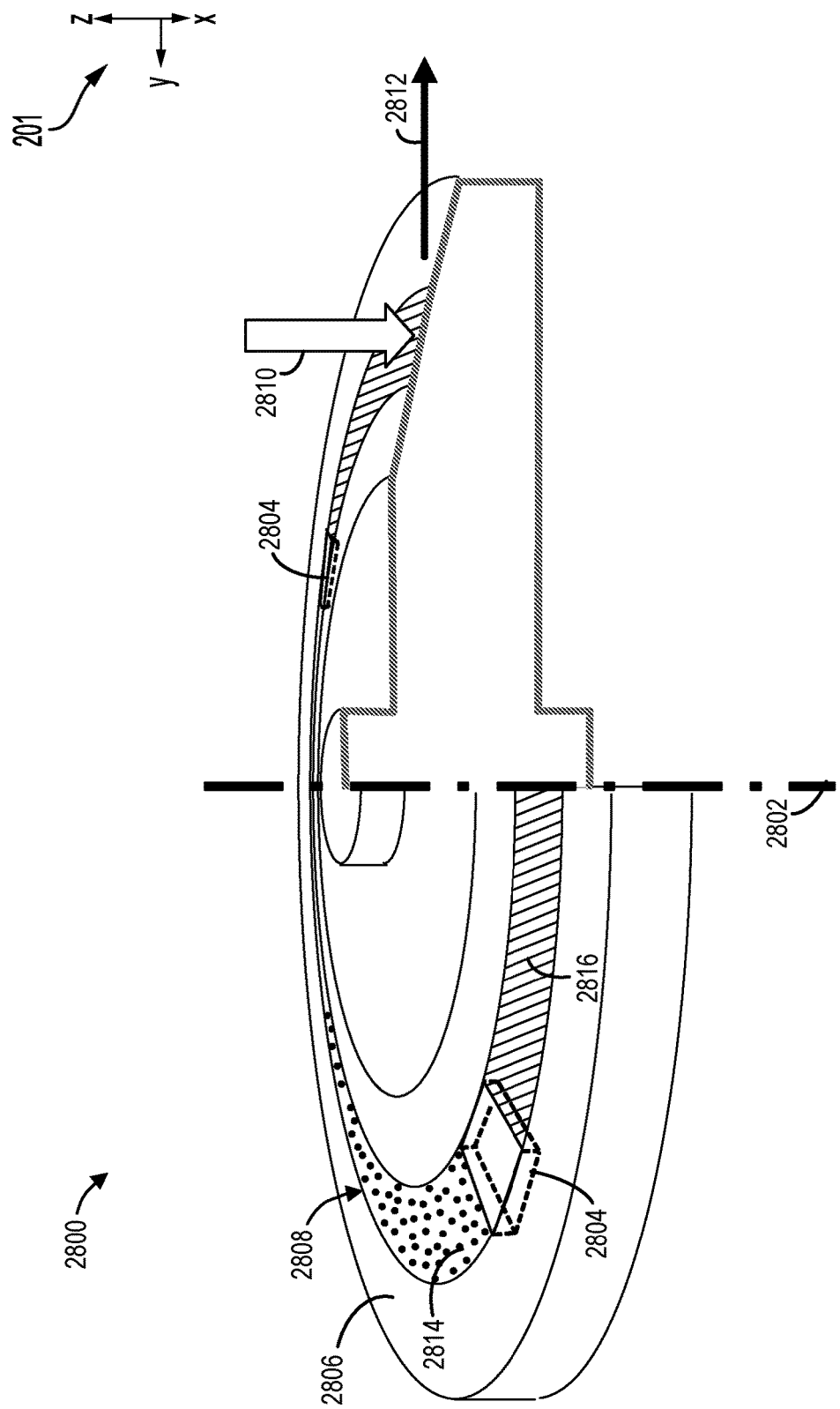
FIG. 28 shows a sixth example of a target for an x-ray tube, from a partial cut-away view, configured for fast kV applications.

The issues described above may be at least partially addressed by configuring the x-ray tube with a target including at least one groove. The target may include more than one material and different spectral filtering may be applied to low versus high tube voltage acquisitions. For example, as shown in FIG. 28, a target 2800 with a central axis 2802 may have grooves 2804 disposed in an upper surface 2806 of the target 2800. The grooves 2804 may be evenly spaced apart along a focal track 2808 of the target 2800.

The target 2800 is shown in FIG. 28 with two grooves 2804, arranged oppositely along the focal track 2808. In other examples, however, the target 2800 may have more or less than two grooves 2804. The grooves 2804 may be cavities or recesses in the upper surface 2806 of the target 2800, along the focal track 2808. A speed of the target 2800 may be synchronized so that an electron beam, as indicated by arrow 2810 interacts with one of the grooves 2804 during a tube voltage transition. When the electron beam strikes one of the grooves 2804 as the target 2800 rotates, generated x-rays may be trapped within the grooves 2804, unable to escape. An x-ray beam, as indicated by arrow 2812, is not emitted at this point during target rotation and in this way, x-ray beams are not emitted towards the subject during transitions between low and high x-ray tube voltage.

In addition, the focal track 2808 of the target 2800 may be equally divided between a first material 2814 and a second material 2816, e.g., half of the focal track 2808 may be formed of the first material 2814 and half of the focal track 2808 may be formed of the second material 2816. While the target 2800 is shown in FIG. 28 with two materials, other examples may include other quantities of different target materials, such as three or four different materials forming the target. Alternatively, the target 2800 may be formed of a single material.

During transitions between the first and second materials 2814, 2816 as the target 2800 rotates, emitted x-ray beams may lead to degraded image quality due to variations in focal spot size, x-ray tube current, etc. By trapping the generated x-rays in the grooves 2804, the x-ray beam is blocked, precluding an effect of transitions on image quality.

In a conventional fast kV system, the x-ray tube voltage is varied between a low voltage and a high voltage to provide two different, overlapping spectra. However, as described above, the switching between voltages may reduce an efficiency of image acquisition by the x-ray tube. When an x-ray tube target is formed of more than one material, such as the target 2800 shown in FIG. 28, the target may similarly generate different spectra without demanding voltage change and/or spectra that exhibit greater spectral differences than used in, for example, fast kV switching. For example, as the target 2800 rotates, the electron beam alternates between striking the first material 2814 and the second material 2816, the materials separated by the grooves 2804. The different materials produce different x-ray spectra using a same beam angle with an equal amount of data acquisition points for each spectrum.

The different materials of the target 2800 may be chosen based on their emission characteristics, such as spectral emission lines and k-edges. In addition, in some instances, different spectral filtering may be applied to views obtained from each portion of the focal track, as defined by the grooves 2804. For example, the target 2800 may be formed of a single material with the grooves 2804 positioned as shown in FIG. 28. The grooves 2804 may define a first half and a second half of the target 2800 relative to a position of the electron beam, as indicated by arrow 2810, as the target 2800 rotates.

Using the known position of the target 2800, e.g., by monitoring rotor phase, a first spectral filter may be applied to data acquired from the first half of the target 2800 and a second spectral filter may be applied to data acquired from the second half of the target 2800. Thus, different spectra may be produced even from a target formed of a single material without the switching x-ray tube voltage and providing similar benefits to fast kV switching.

It will be appreciated that each of beam blocking using grooves, incorporating more than one target material, and differential spectral filtering may be used individually or in combination with one another. For example, an x-ray tube may have a target formed of a single material and have grooves disposed in the target, or may include a target formed of two or more materials, or may have a target formed of a single material without grooves and monitored or controlled to apply different spectral filtering during data collection. In another example, the x-ray tube may have a target with grooves arranged in a focal track between more than one type of target material. In yet another example, the x-ray tube may have a target formed of a single material with grooves and different spectral filters may be applied to individual segments of a focal track that are separated by placement of the grooves along the focal track.

In this way, a rotor for a PMSM of an x-ray tube may have a reduced footprint with fewer individually fabricated components. The smaller footprint of the rotor may allow the rotor to achieve faster boost times with lower current input and reduced heat generation. The rotor may have a core configured to receive magnets, the magnets in the rotor core enabling optimized power efficiency for large airgap motor configurations. The magnets on the rotor core also allow determination of an exact position and speed of the rotor, and thereby a target of the x-ray tube, to be monitored in real-time without relying on additional measurement devices. The magnets may also may mitigate abrasive contact between the sleeve and a shaft of the bearing assembly during x-ray tube operation. Thermal barriers may be included to inhibit heat transfer from a target of the x-ray tube to the magnets. Further benefits may be obtained by forming the rotor core from a non-magnetic material, enabling a retention sleeve and the sleeve of the bearing assembly to be additively manufactured together as a single, continuous part. Manufacturing costs may be reduced by additively manufacturing the integrated rotor core, retention sleeve and bearing assembly sleeve, which may enable preclusion of copper casting and machining in the PMSM, elimination of an isolation transformer, and use of a smaller motor controller.

Additionally, by adapting the rotor core with permanent magnets or sensors, abrasive contact between the sleeve and the shaft of the bearing assembly during deceleration of a rotor for an x-ray tube motor may be reduced, prolonging a useful life of the x-ray tube. The permanent magnets or sensors may allow the determination of the speed and position of the rotor, and therefore a target of the x-ray tube, to be controlled and/or monitored in real-time. The control/monitoring of the speed and position of the rotor allows deceleration of the rotor to be regulated such that rubbing between the sleeve and shaft is minimized. The mechanism providing position and phase information may also be utilized to conduct various operations such as correcting for imperfections in the target, treating target impurities and cracks, and enabling focal spot wobble, z-wobble, and fast kV applications. As a result, image quality may be enhanced without adding complexity and cost to the imaging system.

The technical effect of accurately monitoring rotor speed and position is that deceleration of the rotor is controlled to reduce abrasion between journal bearing components, thereby reducing degradation of the journal bearing. A further technical effect is that image acquisition is synchronized with target rotation, enabling performance of operations and applications to increase image resolution and/or x-ray flux.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The disclosure also provides support for a method for decelerating a rotor of an x-ray tube of an imaging system, comprising: controlling and/or monitoring a speed and a position of the rotor, passing the rotor through a first position where a force exerted on the rotor, is less than Earth's gravitational pull, the force due to a combination of gravity and radial acceleration, and initiating a predefined deceleration profile to decelerate the rotor to a halt when the x-ray tube passes through the first position. In a first example of the method, the method further comprises: rotating a gantry of the imaging system at a speed where the radial acceleration is equal to 1 g prior to passing the rotor through the first position and wherein the rotor is located in the gantry. In a second example of the method, optionally including the first example, initiating the predefined deceleration profile includes estimating a starting position of the gantry to enable the rotor to halt when the x-ray tube passes through the first position. In a third example of the method, optionally including the first and second examples, passing the rotor through the first position includes passing the rotor through a top of the gantry. In a fourth example of the method, optionally including the first through third examples, the method further comprises: continually updating the starting position of the gantry for initiating the predefined deceleration profile based on a feedback loop. In a fifth example of the method, optionally including the first through fourth examples, passing the rotor through the first position maintains a contact layer between a shaft and a sleeve of a bearing of the x-ray tube throughout deceleration of the rotor. In a sixth example of the method, optionally including the first through fifth examples, controlling and/or monitoring the speed and the position of the rotor includes adapting the rotor with permanent magnets. In a seventh example of the method, optionally including the first through sixth examples, monitoring the speed and the position of the rotor includes adapting the rotor with speed and position measurement devices.

The disclosure also provides support for a method for operating an x-ray tube, comprising: controlling and/or monitoring a speed and position of a rotor of the x-ray tube, the speed and position of the rotor provided by configuring the x-ray tube with permanent magnets, and of a target of the x-ray tube, and using the monitored speed and position of the target to perform operations to increase image resolution and/or increase x-ray flux. In a first example of the method, performing the operations includes correcting image data based on a correction factor estimated from an x-ray spectrum emitted from the target of the x-ray tube and wherein the target includes at least one region with imperfections. In a second example of the method, optionally including the first example, performing the operations includes identifying the target as a source of a high voltage instability event when the target has a localized imperfection causing the high voltage instability event. In a third example of the method, optionally including the first and second examples, performing the operations includes determining a location of an impurity on the target and removing the impurity by applying a low x-ray tube current to the impurity. In a fourth example of the method, optionally including the first through third examples, performing the operations includes determining a location of cracks in the target and repairing the cracks by at least one of slow continuous heating and pulsed heating. In a fifth example of the method, optionally including the first through fourth examples, performing the operations includes configuring the target with two or more segments to vary a position of a focal track of the target along an axis perpendicular to a surface of the target and wherein varying the position of the focal track along the axis provides focal spot wobble without electron beam deflection. In a sixth example of the method, optionally including the first through fifth examples, performing the operations includes adapting the target with two or more concentric focal tracks and alternating an interaction of an electron beam with the target between the two or more concentric focal tracks to provide z-wobble. In a seventh example of the method, optionally including the first through sixth examples, performing the operations includes adapting the target with at least one groove configured to trap x-rays emitted by an electron beam striking the target and wherein the x-rays are trapped within the at least one groove when the electron beam interacts with the at least one groove during rotation of the target. In an eighth example of the method, optionally including the first through seventh examples, the method further comprises: adapting the target with two or more materials, the two or more materials each emitting a different x-ray spectrum upon interaction with the electron beam and wherein the electron beam alternates between striking each of the two of more materials as the target rotates.

The disclosure also provides support for a CT imaging system, comprising: a rotating gantry, an x-ray tube coupled to the gantry and having a rotor driving rotation of a target of the x-ray tube, and a control unit including executable instructions stored in non-transitory memory causing the control unit to: control and/or monitor a speed and a position of a rotor of the x-ray tube as provided by configuring the x-ray tube with permanent magnets, control deceleration of the rotor based on the monitored speed and the monitored position, and use the monitored speed and the monitored position of the rotor to conduct operations to enhance image quality and/or increase rotor life. In a first example of the system, the x-ray tube has liquid bearings and the permanent magnets are located in at least one of a bearing assembly and the rotor to enable monitoring of the speed and the position of the rotor in real-time. In a second example of the system, optionally including the first example, a speed and a position of the target is known based on the monitored speed and the monitored position of the rotor and wherein controlling the speed and position of the rotor adjusts the speed and position of the target relative to an electron beam striking the target.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for operating an x-ray tube, comprising:
controlling and/or monitoring a speed and position of a rotor of the x-ray tube, the speed and position of the rotor provided by configuring the x-ray tube with permanent magnets, and of a target of the x-ray tube; and
using the monitored speed and position of the target to perform operations to increase useful x-ray tube life, increase image resolution, and/or increase x-ray flux.

2. The method of claim 1, wherein performing the operations includes correcting image data based on a correction factor estimated from an x-ray spectrum emitted from the target of the x-ray tube and wherein the target includes at least one region with imperfections.

3. The method of claim 1, wherein performing the operations includes identifying the target as a source of a high voltage instability event when the target has a localized imperfection causing the high voltage instability event.

4. The method of claim 1, wherein performing the operations includes determining a location of an impurity on the target and removing the impurity by applying a low x-ray tube current to the impurity.

5. The method of claim 1, wherein performing the operations includes determining a location of cracks in the target and repairing the cracks by at least one of slow continuous heating and pulsed heating.

6. The method of claim 1, wherein performing the operations includes configuring the target with two or more segments to vary a position of a focal track of the target along an axis perpendicular to a surface of the target and wherein varying the position of the focal track along the axis provides focal spot wobble without electron beam deflection.

7. The method of claim 1, wherein performing the operations includes adapting the target with two or more concentric focal tracks and alternating an interaction of an electron beam with the target between the two or more concentric focal tracks to provide z-wobble.

8. The method of claim 1, wherein performing the operations includes adapting the target with at least one groove configured to trap x-rays emitted by an electron beam striking the target and wherein the x-rays are trapped within the at least one groove when the electron beam interacts with the at least one groove during rotation of the target.

9. The method of claim 8, further comprising adapting the target with two or more materials, the two or more materials each emitting a different x-ray spectrum upon interaction with the electron beam and wherein the electron beam alternates between striking each of the two of more materials as the target rotates.

10. A CT imaging system, comprising:
a rotating gantry;
an x-ray tube coupled to the gantry and having a rotor driving rotation of a target of the x-ray tube; and
a control unit including executable instructions stored in non-transitory memory causing the control unit to:
control and/or monitor a speed and a position of a rotor of the x-ray tube as provided by configuring the x-ray tube with permanent magnets;
control deceleration of the rotor based on the monitored speed and the monitored position; and
use the monitored speed and the monitored position of the rotor to conduct operations to enhance image quality and/or increase rotor life.

11. The CT imaging system of claim 10, wherein the x-ray tube has liquid bearings and the permanent magnets are located in at least one of a bearing assembly and the rotor to enable monitoring of the speed and the position of the rotor in real-time.

12. The CT imaging system of claim 10, wherein a speed and a position of the target is known based on the monitored speed and the monitored position of the rotor and wherein controlling the speed and position of the rotor adjusts the speed and position of the target relative to an electron beam striking the target.

* * * * *